(12) United States Patent
Nakajima et al.

(10) Patent No.: US 12,226,161 B2
(45) Date of Patent: Feb. 18, 2025

(54) OPHTHALMIC APPARATUS

(71) Applicant: Topcon Corporation, Tokyo (JP)

(72) Inventors: Masashi Nakajima, Ageo (JP); Jonathan Liu, Tokyo (JP); Yasufumi Fukuma, Wako (JP)

(73) Assignee: TOPCON CORPORATION, Tokyo (JP)

( * ) Notice: Subject to any disclaimer, the term of this patent is extended or adjusted under 35 U.S.C. 154(b) by 780 days.

(21) Appl. No.: 17/375,026

(22) Filed: Jul. 14, 2021

(65) Prior Publication Data

US 2021/0338076 A1 Nov. 4, 2021

Related U.S. Application Data

(63) Continuation of application No. PCT/JP2020/000502, filed on Jan. 9, 2020.

(30) Foreign Application Priority Data

Jan. 16, 2019 (JP) .................... 2019-005431

(51) Int. Cl.
*A61B 3/00* (2006.01)
*A61B 3/10* (2006.01)
(Continued)

(52) U.S. Cl.
CPC .......... *A61B 3/103* (2013.01); *A61B 3/0041* (2013.01); *A61B 3/0091* (2013.01); *A61B 3/102* (2013.01); *A61B 3/12* (2013.01)

(58) Field of Classification Search
CPC ..... A61B 3/028; A61B 3/0025; A61B 3/0016; A61B 3/1225; A61B 3/12; A61B 3/117;
(Continued)

(56) References Cited

U.S. PATENT DOCUMENTS

| 8,814,356 B2 | 8/2014 | Ehrmann et al. |
| 2009/0161090 A1* | 6/2009 | Campbell ............ G01B 11/25 351/212 |

(Continued)

FOREIGN PATENT DOCUMENTS

| CN | 102939044 A | 2/2013 |
| CN | 103142210 A | 6/2013 |

(Continued)

OTHER PUBLICATIONS

EPO translation CN103142210 (Year: 2024).*
(Continued)

*Primary Examiner* — Travis S Fissel
(74) *Attorney, Agent, or Firm* — XSENSUS LLP

(57) ABSTRACT

An ophthalmic apparatus includes an acquiring unit, an OCT unit, an analyzer, and a calculator. The acquiring unit is configured to acquire a dioptric power in a first region including a fovea of a subject's eye. The OCT unit is configured to acquire OCT data of a fundus of the subject's eye using optical coherence tomography. The analyzer is configured to specify a shape of the fundus by analyzing the OCT data. The calculator is configured to calculate a dioptric power in a peripheral region of the first region of the fundus based on the dioptric power in the first region and the shape of the fundus.

19 Claims, 12 Drawing Sheets

(51) Int. Cl.
*A61B 3/103* (2006.01)
*A61B 3/12* (2006.01)

(58) Field of Classification Search
CPC ....... A61B 3/1035; A61B 3/103; A61B 3/102; A61B 3/10; A61B 3/0041; A61B 3/0091; A61B 3/1005; A61B 3/107
USPC ................................ 351/206, 205, 246, 212
See application file for complete search history.

(56) References Cited

U.S. PATENT DOCUMENTS

| | | |
|---|---|---|
| 2009/0244485 A1 | 10/2009 | Walsh et al. |
| 2009/0257026 A1 | 10/2009 | Varnas et al. |
| 2010/0225014 A1 | 9/2010 | Bille |
| 2010/0228345 A1 | 9/2010 | Bille |
| 2011/0128500 A1 | 6/2011 | Bille |
| 2011/0128501 A1 | 6/2011 | Bille |
| 2011/0130654 A1 | 6/2011 | Bille |
| 2011/0130677 A1 | 6/2011 | Bille |
| 2011/0210459 A1 | 9/2011 | Bille |
| 2011/0212205 A1 | 9/2011 | Bille |
| 2011/0299034 A1 | 12/2011 | Walsh et al. |
| 2012/0140174 A1 | 6/2012 | Hee et al. |
| 2013/0100409 A1 | 4/2013 | Grant et al. |
| 2013/0103144 A1 | 4/2013 | Bille et al. |
| 2013/0201449 A1 | 8/2013 | Walsh et al. |
| 2014/0084501 A1 | 3/2014 | Bille |
| 2014/0111766 A1 | 4/2014 | Umekawa et al. |
| 2015/0076723 A1 | 3/2015 | Bille |
| 2015/0085253 A1 | 3/2015 | Walsh et al. |
| 2015/0112203 A1 | 4/2015 | Bille |
| 2015/0138503 A1 | 5/2015 | Walsh et al. |
| 2017/0049318 A1 | 2/2017 | Walsh et al. |
| 2017/0119247 A1 | 5/2017 | Walsh et al. |
| 2017/0127931 A1* | 5/2017 | Utsunomiya ............ A61B 3/12 |
| 2017/0215725 A1* | 8/2017 | Ishiai .................... A61B 3/152 |
| 2017/0245756 A1 | 8/2017 | Hayashi et al. |
| 2018/0279872 A1 | 10/2018 | Okamoto et al. |
| 2019/0090733 A1 | 3/2019 | Walsh et al. |
| 2020/0085294 A1 | 3/2020 | Everett et al. |
| 2021/0121061 A1 | 4/2021 | Okamoto et al. |

FOREIGN PATENT DOCUMENTS

| | | | |
|---|---|---|---|
| CN | 103314270 A | | 9/2013 |
| CN | 103767674 A | | 5/2014 |
| CN | 103142210 B | * | 3/2015 |
| CN | 105608314 A | | 5/2016 |
| CN | 106963338 A | | 7/2017 |
| EP | 3075303 A1 | | 10/2016 |
| EP | 3384826 A2 | | 10/2018 |
| JP | 2014-79495 A | | 5/2014 |
| JP | 2016-77774 A | | 5/2016 |
| JP | 2018-164636 A | | 10/2018 |
| JP | 2018-187431 A | | 11/2018 |
| WO | 2010/117386 A1 | | 10/2010 |
| WO | 2016/060033 A1 | | 4/2016 |
| WO | 2018/178269 A1 | | 10/2018 |

OTHER PUBLICATIONS

Extended European Search Report issued Aug. 22, 2022 in corresponding European Patent Application No. 20741052.3, 6 pages.
Smith et al. "Relative Peripheral Hyperopic Defocus Alters Central Refractive Development in Infant Monkeys", Vision Res., vol. 49, No. 19, Sep. 2009, pp. 2386-2392.
Office Action mailed on Nov. 4, 2020, received for CN Application 202080000706.1, 10 pages including English Translation.
Notice of Reasons for Refusal mailed on Mar. 31, 2020, received for JP Application 2020-512624 4 pages including English Translation.
International Search Report and Written Opinion mailed on Mar. 10, 2020, received for PCT Application PCT/JP2020/000502, Filed on Jan. 9, 2020, 8 pages including English Translation.

* cited by examiner

OPHTHALMIC APPARATUS

CROSS-REFERENCE TO RELATED APPLICATIONS

The present application is a continuation application of International Patent Application No. PCT/JP2020/000502, filed Jan. 9, 2020, which claims priority to Japanese Patent Application No. 2019-005431, filed Jan. 16, 2019. The contents of these applications are incorporated herein by reference in their entirety.

FIELD

The disclosure relates to an ophthalmic apparatus.

BACKGROUND

When humans look at an object, light reflected from the object and entering an eye shines on the vicinity of the center of the retina (specifically, a fovea), the light is converted into electrical signals in the retina, and the electrical signals are transmitted to the brain (central vision). When humans try to look at the object by shining light on the peripheral visual field outside the vicinity of the center of the retina, humans rotate the eyeball around the center of rotation of the eye or turn the face. In other words, the resolution of the peripheral visual field is physiologically low, and the demand for obtaining an accurate refractive power of the peripheral visual field is low in daily life.

Meanwhile, in recent years, as one cause of myopia progression, it has been reported the possibility that myopia progresses as the retina tries to extend backward due to the fact that the focal point of the peripheral visual field is located further back (scleral side) with respect to the retinal surface (e.g., Earl L. Smith et al., "Relative peripheral hyperopic defocus alters central refractive development in infant monkeys", Vision Research, September 2009, 49(19), pp. 2386-2392). In other words, from the viewpoint of suppressing the myopia progression, the demand for accurately determining the refractive power of the peripheral visual field may increase in the future.

Further, in order to suppress the myopia progression, eyeglasses and contact lenses have been developed. The eyeglasses and the contact lenses move the focal position of the central visual field to the near side (cornea side) by increasing the refractive power of the peripheral visual field. Further, refractive surgeries such as the wavefront-guided LASIK are also performed. Here, the wavefront-guided LASIK is performed based on wavefront aberration measured in advance. Therefore, in such advanced refractive correction, the demand for accurately measuring the refractive power of the peripheral visual field may increase even more.

For example, Japanese Unexamined Patent Publication No. 2016-077774 discloses an ophthalmic apparatus capable of measuring such a refractive power of the eye. The ophthalmic apparatus disclosed in Japanese Unexamined Patent Publication No. 2016-077774 is capable of performing a subjective inspection and an objective measurement. The subjective inspection is a subjective test for determining a dioptric power of a subject's eye in accordance with a response of the subject to the optotype (Landolt ring, etc.) presented to the subject's eye. The objective measurement is an objective test for determining a dioptric power of the subject's eye based on changes in the size or the shape of an image of reflected light of light projected onto a fundus of the subject's eye.

SUMMARY

One aspect of some embodiments is an ophthalmic apparatus, including: an acquiring unit configured to acquire a dioptric power in a first region including a fovea of a subject's eye; an OCT unit configured to acquire OCT data of a fundus of the subject's eye using optical coherence tomography; an analyzer configured to specify a shape of the fundus by analyzing the OCT data; and a calculator configured to calculate a dioptric power in a peripheral region of the first region of the fundus based on the dioptric power in the first region and the shape of the fundus.

Another aspect of some embodiments is an ophthalmic apparatus, including: a refraction measurement unit configured to objectively measure a dioptric power in a predetermined region on a fundus of a subject's eye; an OCT unit configured to acquire OCT data of the fundus using optical coherence tomography; an analyzer configured to specify a shape of the fundus by analyzing the OCT data; and a calculator configured to calculate the dioptric power in the predetermined region on the fundus based on the shape of the fundus.

DETAILED DESCRIPTION

Figure 1:
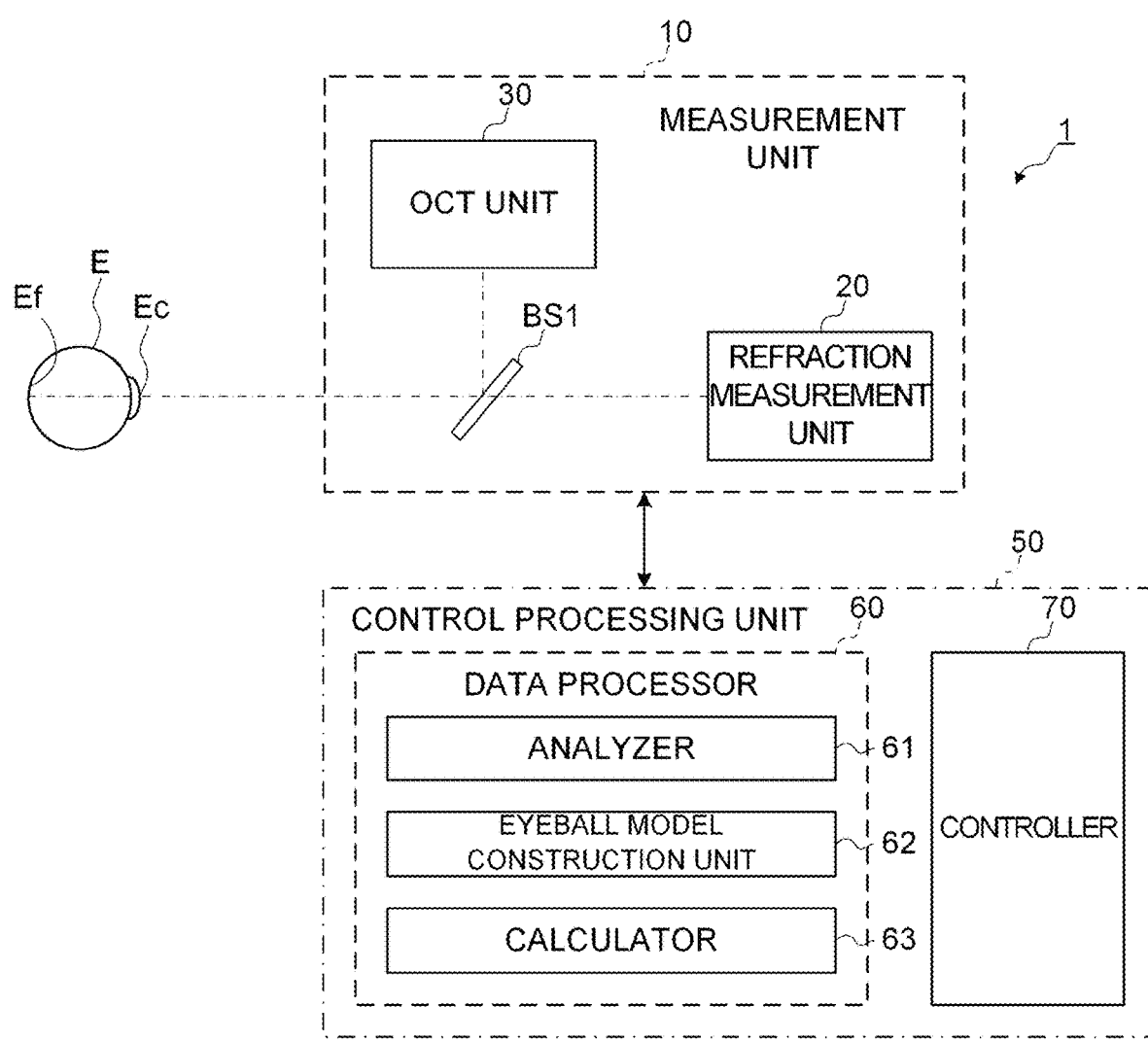
FIG. 1 is a schematic diagram illustrating an example of a configuration of an ophthalmic apparatus according to a first embodiment.

In general, a fixation target is projected onto a measurement optical axis in ophthalmic apparatuses. Thereby, a dioptric power in the vicinity of the fovea of the retina can be measured. Thus, a dioptric power in a peripheral region outside a region including the fovea can not be measured. In such a ophthalmic apparatus, by projecting the fixation target onto the peripheral region, the dioptric power in the peripheral region can be measured.

However, in case of projecting a ring-shaped light flux onto the fundus and detecting returning light of the ring-shaped light flux, the returning light is affected by the shape of the fundus. Thus, the dioptric power can not be measured with high accuracy. Further, the light is projected onto a region having a predetermined size on the fundus. Thus, a local dioptric power on the fundus can not be measured. In the same way, in case of projecting light using a rotary prism, the returning light is affected by the shape of the fundus. Thus, the dioptric power can not be measured with high accuracy.

According to some embodiments of the present invention, an ophthalmic apparatus capable of obtaining a dioptric power in a predetermined region on a fundus of a subject's eye with high accuracy can be provided.

Referring now to the drawings, exemplary embodiments of an ophthalmic apparatus according to the present invention are described below. Any of the contents of the documents cited in the present specification and arbitrary known techniques may be applied to the embodiments below.

An ophthalmic apparatus according to embodiments is capable of obtaining a local dioptric power (refractivity, refractive power) on a fundus of a subject's eye. The ophthalmic apparatus according to some embodiments acquires a dioptric power in a region including a fovea of the subject's eye and OCT data of the fundus, analyzes the acquired OCT data to specify a shape of the fundus, and calculates (i.e., estimates) a dioptric power in a peripheral region outside the region including the fovea based on the acquired dioptric power and the specified shape of the fundus. In some embodiments, distribution information on dioptric powers in the region including the fovea or distribution information on dioptric powers in the peripheral region is generated.

The ophthalmic apparatus according to some embodiments performs objective refraction measurement and OCT measurement on a predetermined region on the fundus. The predetermined region is a central region including the fovea of the subject's eye or a peripheral region outside the central region. And, the ophthalmic apparatus analyzes the OCT data, the OCT data being acquired by performing OCT measurement, to specify the shape of the fundus, corrects a light receiving image, the light receiving image being obtained by performing objective refraction measurement, based on the shape of the fundus, and calculates a dioptric power in the predetermined region based on the corrected light receiving image.

The dioptric power is acquired by performing objective refraction measurement using an objective refraction measurement apparatus, for example. In some embodiments, the dioptric power is acquired by receiving dioptric power data from an electronic health record system, etc. In the same way, the OCT data is acquired by performing measuring using an OCT apparatus, for example. In the measurement, OCT scan and image data construction are performed. In some embodiments, the OCT data is acquired from the electronic health record system, a medical image archiving system, an external apparatus, or the like.

The ophthalmic apparatus can calculate the dioptric power of the above region using parameter of an eyeball model such as a known schematic eye. The parameter is a parameter representing optical characteristics of the eyeball. Examples of the parameter include axial length data, anterior chamber depth data, crystalline lens shape data representing a shape of a crystalline lens, corneal shape data representing a shape of a cornea. Examples of the crystalline lens shape data include a curvature of crystalline lens and a thickness of crystalline lens. Examples of the corneal shape data includes a corneal curvature radius and a corneal thickness.

The ophthalmic apparatus can construct a new eyeball model by replacing a part of the parameter of the eyeball model with an actual measurement value of the subject's eye, and can calculate the dioptric power of the above region using the constructed new eyeball model. The above parameter(s) can be acquired by analyzing the OCT data. In some embodiments, the above parameter is obtained from an electronic health record system, a medical image archiving system, an external apparatus, or the like.

The ophthalmic apparatus according to some embodiments includes at least one of an objective refraction measurement apparatus and an OCT apparatus. The ophthalmic apparatus according to some embodiments includes a device that receives data from an external apparatus or a recording medium. Examples of the device include a communication interface and an input/output interface.

In other words, the ophthalmic apparatus according to the embodiments may be, for example, any one of the following: (A) an inspection apparatus that includes an objective refraction measurement apparatus (refraction measurement unit) and an OCT apparatus (OCT unit): (B) an inspection apparatus that does not include an OCT apparatus (OCT unit) but includes an objective refraction measurement (refraction measurement unit): (C) an inspection apparatus that does not include an objective refraction measurement (refraction measurement unit) but includes an OCT apparatus (OCT unit): (D) an information processing apparatus that includes neither an objective refraction measurement apparatus (refraction measurement unit) nor an OCT apparatus (OCT) unit.

The ophthalmic apparatus according to the embodiments can include one or more processors and perform various types of data processing. Examples of data processing include analysis processing for the OCT data, calculation processing of the dioptric power based on the detection result obtained by the objective refraction measurement, and calculation processing of the dioptric power reflecting the shape of the fundus. In some embodiments, the data processing includes correction processing for the detection result obtained by performing objective refraction measurement.

In this specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes, for example, the specific function by reading out a program stored in a storage circuit or a storage device and executing the program.

First Embodiment

The ophthalmic apparatus according to the first embodiment calculates (i.e., estimates) a dioptric power in a peripheral region outside a central region on the fundus from the dioptric power in the central region including a fovea on the fundus of the subject's eye and the shape of the fundus.

<Configuration>

FIG. 1 shows an example of a configuration of the ophthalmic apparatus according to the first embodiment. The ophthalmic apparatus 1 according to the first embodiment is an inspection apparatus that includes an objective refraction measurement apparatus (refraction measurement unit) and an OCT apparatus (OCT unit). The ophthalmic apparatus 1 includes a measurement unit 10, a control processing unit 50. The measurement unit 10 includes a refraction measurement unit 20, an OCT unit 30, and a beam splitter BS1. The control processing unit 50 includes a data processor 60 and a controller 70. The data processor 60 includes an analyzer 61, an eyeball model construction unit 62, and a calculator (estimation unit) 63.

The refraction measurement unit 20 objectively measures a dioptric power of a subject's eye E. The refraction measurement unit 20 has the same configuration as a known refractometer, for example. An exemplary refractometer (not shown in the figure) includes a projection system, a light receiving system, and a processor, as disclosed in Japanese Unexamined Patent Publication No. 2016-077774.

A projection system of the refraction measurement unit 20 is configured to project light emitted from a light source onto a fundus Ef of the subject's eye E. The projection system projects the light from the light source onto the fundus Ef through a collimator lens, a focusing lens, a relay lens, a pupil lens, a perforated prism, a decentered prism (eccentric prism), an objective lens, and the like, for example.

A light receiving system of the refraction measurement unit 20 projects reflected light from the fundus Ef onto an imaging element through the objective lens, the decentered prism, the perforated prism, other pupil lenses, other relay lenses, another focusing lens, a conical prism, an imaging lens, and the like. Thereby, a ring pattern image formed on an imaging surface of the imaging element is detected.

In some embodiments, the refraction measurement unit 20 is configured to project ring-shaped light onto the fundus Ef and to detect the ring pattern image formed by the reflected light from the fundus Ef. In some embodiments, the refraction measurement unit 20 is configured to project bright spot onto the fundus Ef, to convert the reflected light from the fundus Ef into ring-shaped light, and to detect the ring pattern image formed by the converted ring-shaped light.

The processor of the refraction measurement unit 20 processes the output from the imaging element of the light receiving system to calculate the dioptric power.

In some embodiments, the processor executes a process of specifying an elliptical shape by elliptically approximating the ring pattern image acquired by the imaging element and a process of obtaining the dioptric power (measurement data) based on the specified elliptical shape and a diopter for focus adjustment for the focusing lens and the like, for example.

In some embodiments, the processor executes a process of obtaining brightness distribution in the image depicting the ring pattern image acquired by the imaging element, a process of obtaining a position of the center of gravity of the ring pattern image from the obtained brightness distribution, a process of obtaining brightness distribution along a plurality of scanning directions extending radially from the obtained position of the center of gravity, a process of specifying a ring pattern image from the obtained brightness distribution along the plurality of scanning directions, a process of obtaining an approximate ellipse from the specified ring pattern image, and a process of calculating the dioptric power by substituting the major axis and the minor axis of the obtained approximate ellipse into a known expression, for example.

In some embodiments, the processor executes a process of obtaining a deflection (position shift, deformation, etc.) of the ring pattern image acquired by the imaging element with reference to the reference pattern, and a process of obtaining the dioptric power from this deflection, for example.

In some embodiments, a spherical power S, an astigmatic power C, and an astigmatic axis angle A are calculated as the dioptric power. In some embodiments, an equivalent spherical power SE (S+C/2) is calculated as the dioptric power.

The OCT unit 30 acquires OCT data by applying OCT scan to the fundus Ef. The OCT data may be interference signal data, reflection intensity profile data obtained by applying Fourier transformation to the interference signal data, or image data obtained by imaging the reflection intensity profile data. In the following, an image acquired by using OCT may be referred to as an OCT image.

The OCT method that can be performed by the OCT unit 30 is typically Fourier domain OCT. Fourier domain OCT may be either spectral domain OCT or swept source OCT. The swept source OCT is a method that splits light from a wavelength tunable light source into measurement light and reference light; superposes returning light of the measurement light projected onto the subject's eye with the reference light to generate interference light; detects the interference light with an optical detector; and applies the Fourier transformation etc. to detection data (interference signal data) acquired in accordance with the sweeping of wavelengths and the scanning of the measurement light to form reflection intensity profile data. On the other hand, the spectral domain OCT is a method that splits light from a low coherence light source (broadband light source) into measurement light and reference light; superposes returning light of the measurement light projected onto the subject's eye with the reference light to generate interference light; detects the spectral distribution of the interference light with a spectrometer; and applies the Fourier transformation etc. to detection data (interference signal data) detected by the spectrometer to form reflection intensity profile data. In other words, the swept source OCT is an OCT method for acquiring the spectral distribution by time division, and the spectral domain OCT is an OCT method for acquiring the spectral distribution by space division.

The OCT unit 30 has the same configuration as a known OCT apparatus, for example. An exemplary OCT apparatus (not shown in the figure) includes a light source, an interference optical system, a scan system, a detection system, and a processor, as disclosed in Japanese Unexamined Patent Publication No. 2016-077774.

Light emitted from the light source is split into the measurement light and the reference light by the interference optical system. The reference light is guided to a reference arm. The measurement light is projected onto the fundus Ef through a measurement arm. The measurement arm is provided with the scan system. The scan system includes, for example, an galvano scanner and is capable of deflecting the measurement light one-dimensionally or two-dimensionally. The scan system deflects the measurement light according to a predetermined scan mode.

The measurement light projected onto the fundus Ef is scattered and reflected at various depth positions (layer boundaries, etc.) of the fundus Ef. The returning light of the measurement light from the subject's eye E is combined with the reference light by the interference optical system. The returning light of the measurement light and the reference light generates the interference light according to the principle of superposition. This interference light is detected by the detection system. The detection system typically includes the spectrometer in case of spectral domain OCT. The detection system typically includes a balanced photodiode and a data acquisition system (DAQ) in case of swept source OCT.

The processor of the OCT unit 30 constructs OCT data based on detection data detected by the detection system of the OCT unit 30. Typically, the OCT data is image data. Similar to conventional OCT data processing, the processor constructs the reflection intensity profile data in each A-line by applying filter processing, fast Fourier transformation (FFT), and the like to the detection data. Here, the A-line corresponds to a path of the measurement light in the subject's eye E. In addition, the processor constructs the image data of each A-line by applying image processing (image expression) to this reflection intensity profile data. Here, the image data of A-line is A-scan data.

The processor can control the scan system according to the scan mode. Examples of the scan mode include a line scan, a raster scan (three-dimensional scan), a circle scan, a concentric scan, a radial scan, a cross scan, a multi cross scan. The line scan is a scan pattern along a linear trajectory. The raster scan is a scan pattern consisting of a plurality of line scans arranged parallel to one another. The circle scan is a scan pattern along a circular trajectory. The concentric scan is a scan pattern consisting of a plurality of circle scans arranged concentrically. The radial scan is a scan pattern consisting of a plurality of line scans arranged radially. The cross scan is a scan pattern consisting of two line scans arranged orthogonal to one another. The multi cross scan is a scan pattern consisting of two line scan groups orthogonal to one another. Each groups includes five lines parallel to one another, for example.

The processor can construct B-scan data by arranging a plurality of A-scan data according to the scan mode performed by the scan system. The processor can construct stack data by arranging a plurality of B-scan data according to the scan mode performed by the scan system. The processor can construct volume data or voxel data from the stack data. The processor can render the stack data or the volume data. Examples of rendering method include volume rendering, multi-planar reconstruction (MPR), surface rendering, and projection.

Further, the processor can form a B-mode image in an arbitrary cross section, a C-mode image in an arbitrary cross section, a projection image, a shadowgram, and the like, by performing various renderings on the volume data acquired as describe above or the stack data acquired as described above. Examples of the B-mode image include a longitudinal cross-sectional image and an axial cross-sectional image. Examples of the C-mode image includes a transverse section image and a horizontal cross-sectional image. The volume data or the stack data is a three-dimensional data set. An image in an arbitrary cross section such as a B-mode image or a C-mode image is formed by selecting pixels (voxels) on a designated cross section from the three-dimensional data set. The projection image is formed by projecting the three-dimensional data set in a predetermined direction. Examples of the predetermined direction include a traveling direction of the measurement light, depth direction, and axial direction. The shadowgram is formed by projecting a part of the three-dimensional data set in a predetermined direction. Examples of the part of the three-dimensional data set include partial data corresponding to a specific layer. An image having a viewpoint on the front side of the subject's eye, such as the C-mode image, the projection image, and the shadowgram, is called a front image (en-face image).

The beam splitter BS1 coaxially couples an optical path of the optical system (interference optical system, etc.) of the OCT unit 30 with an optical path of the optical system (projection system and light receiving system) of the refraction measurement unit 20. For example, a dichroic mirror is used as the beam splitter BS1.

In some embodiments, the ophthalmic apparatus 1 has a function of presenting a fixation target to the subject's eye E. The fixation target is used for guiding a visual line of the subject's eye E. The fixation target may be an internal fixation target presented to the subject's eye E or an external fixation target presented to the fellow eye. In some embodiments, an optical path of an fixation projection system and the optical path of the interference optical system of the OCT unit 30 are configured to coaxially coupled using an optical path coupling member arranged between the OCT unit 30 and the beam splitter BS1. Examples of the optical path coupling member include a beam splitter.

A projection position of the fixation target on the fundus Ef projected by the fixation target projection system can be changed. In some embodiments, the fixation target is projected onto the measurement optical axes of coaxially coupled the optical system of the refraction measurement unit 20 and the optical system of the OCT unit 30. In some embodiments, the fixation target is projected at a position deviated from the measurement optical axis on the fundus Ef.

The control processing unit 50 performs various calculations and various controls for operating the ophthalmic apparatus 1. The control processing unit 50 includes one or more processors and one or more storage devices. Examples of the storage device include a random access memory (RAM), a read only memory (ROM), a hard disk drive (HDD), a solid state drive (SSD). The storage device stores various computer programs. The calculation and control for the present example are realized by the processor operating based on the computer program(s).

The functions of the data processor 60 and the controller 70 in the control processing unit 50 are realized by the one or more processors. In some embodiments, the function of the data processor 60 is realized by a data processor and the function of the controller 70 is realized by a control processor.

The data processor 60 executes various kind of data processing. For example, the data processor 60 can execute segmentation processing and calculation processing. In the segmentation processing, a specific tissue or a specific tissue boundary is obtained using the OCT data. In the calculation processing, a size such as a layer thickness or a volume of the tissue or a distance between predetermined sites is obtained. Further, the data processor 60 calculates the dioptric power in the peripheral region from the dioptric power in the central region including the fovea and the shape of the fundus Ef, using parameter(s) of an eyeball model. Here, the dioptric power in the central region is acquired by the refraction measurement unit 20. The shape of the fundus Ef is specified by performing segmentation processing.

The analyzer 61 specifies a predetermined layer region of the fundus Ef by analyzing the OCT data acquired by OCT unit 30. Examples of the layer region of the fundus Ef include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, the choroid, the sclera, and the boundary surfaces of each layer region.

Processing for specifying the predetermined layer region from the OCT data typically includes the segmentation processing. The segmentation processing is known processing for specifying a partial region in an image data. The analyzer 61 performs, for example, the segmentation processing based on brightness values in the OCT image data. That is, each of the layer regions of the fundus Ef has a characteristic reflectance, and image regions corresponding to these layer regions also have characteristic brightness values. The analyzer 61 can specify a target image region (layer region) by performing the segmentation processing based on these characteristic brightness values. For example, the analyzer 61 can specify an OS-RPE boundary surface with highest brightness value.

Further, the analyzer 61 can calculate a predetermined intraocular distance based on the OCT data acquired by the OCT unit 30. For example, the analyzer 61 specifies peak positions of the detection result (interference signal) of the interference light corresponding to the predetermined sites in the eye by analyzing the OCT data, and obtains the intraocular distance based on the distance between the specified peak positions. For example, the analyzer 61 obtains the intraocular distance (distance between layers) based on the number of pixels and a predetermined spacing correction value. The number of pixels is the number existing between the two layer regions obtained by performing segmentation processing. The measurement for the intraocular distance is performed along a predetermined direction. The measurement direction of the intraocular distance may be, for example, a direction determined by OCT scan, or a direction determined based on the OCT data. Examples of the direction determined by OCT scan include the traveling direction of the measurement light. Examples of the direction determined based on the OCT data include the direction orthogonal to the layer. Further, the distance data may be distance distribution data between the two layer regions, a statistic value calculated from this distance distribution data, or distance data between representative points in each layer region. Examples of the static value include an average, a maximum value, a minimum value, a median, a mode, a variance, and a standard deviation.

Examples of the intraocular distance that can be calculated by the analyzer 61 include an axial length, a corneal thickness, an anterior chamber depth, a thickness of the crystalline lens, a length of vitreous cavity, a retinal thickness, and a choroidal thickness.

Further, the analyzer 61 can calculate various parameters representing optical characteristics of the eyeball using the obtained intraocular distance.

The eyeball model construction unit 62 construct an eyeball model. The eyeball model construction unit 62 can construct a new eyeball model by applying separately acquired parameter(s) to an eyeball model such as a known schematic eye. Further, the eyeball model construction unit 62 can construct a new eyeball model by applying the intraocular distance of the subject's eye E acquired by analyzer 61 as the measured parameter to an eyeball model such as a known schematic eye.

The analyzer 61 (or the eyeball model construction unit 62) can specify the shape of the fundus Ef using the constructed eyeball model. For example, the analyzer 61 (or the eyeball model construction unit 62) specifies the shape of the fundus Ef by obtaining a difference of the depth positions between the central region on the fundus Ef and the peripheral region on the fundus Ef.

The calculator 63 calculates the dioptric power in the peripheral region outside the central region including the fovea in the fundus Ef. At this time, the calculator 63 calculates the dioptric power in the peripheral region based on the dioptric power in the central region and the specified shape of the fundus Ef. The dioptric power in the central region is acquired by the refraction measurement unit 20. The calculator 63 can calculate the dioptric power in the peripheral region using the parameter(s) of the eyeball model constructed by the eyeball model construction unit 62.

In some embodiments, the functions of the analyzer 61, the eyeball model construction unit 62, and the calculator 63 are realized by one or more processors. In some embodiments, the function of each of the analyzer 61, the eyeball model construction unit 62, and the calculator 63 is realized by a single processor.

The controller 70 controls each part of the ophthalmic apparatus 1. The controller 70 includes a storage unit (now shown), and can store various types of information. Examples of the information stored in the storage unit include a program for controlling each part of the ophthalmic apparatus 1, information on the subject, information on the subject's eye, measurement data acquired by the measurement unit 10, and processing results acquired by the data processor 60. The function of the controller 70 is realized by a processor.

The controller 70 can control a display device (not shown). Upon receiving control of the controller 70, the display device displays information, as a part of user interface. The display device may be, for example, a liquid crystal display (LCD), or an organic light-emitting diode (OLED) display.

The controller 70 can control the ophthalmic apparatus 1 in accordance with a signal from an operation device (not shown). The operation device functions as a part of the user interface unit. The operation device may include various types of hardware keys (the joystick, buttons, switches, etc.) provided in the ophthalmic apparatus 1. Further, the operation device may include various types of peripheral devices (keyboard, mouse, joystick, operation panel, etc.) connected to the ophthalmic apparatus 1. Further, the operation device may include various kinds of software keys (buttons, icons, menus, etc.) displayed on the touch panel.

The refraction measurement unit 20 is an example of the "acquisition unit" according to the embodiments. The OCT unit 30 is an example of the "acquisition unit" acquiring the OCT data according to the embodiments.

Operation Example

The operation of the ophthalmic apparatus 1 according to the first embodiment will be described.

Figure 2:
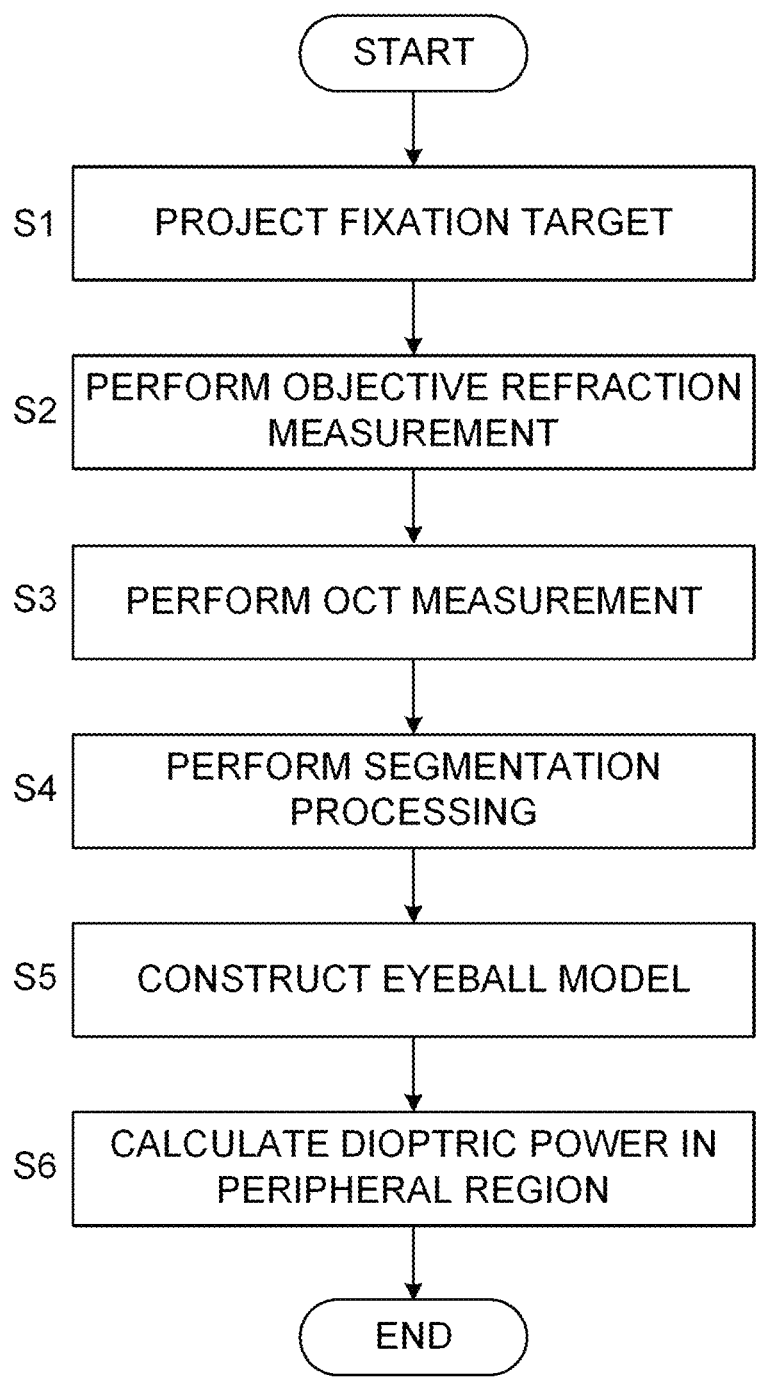
FIG. 2 is a flow chart illustrating an example of an operation of the ophthalmic apparatus according to the first embodiment.

FIG. 2 illustrates an example of the operation of the ophthalmic apparatus 1. FIG. 2 represents a flowchart of an example of the operation of the ophthalmic apparatus 1. The storage unit in the controller 70 stores the computer program for realizing the processing shown in FIG. 2. The controller 70 operates according to the computer program, and thereby the controller 70 executes the processing shown in FIG. 2.

(S1: Project Fixation Target)

First, the controller 70 controls the fixation projection system (not shown) to project the fixation target on the measurement optical axis of the optical system of the refraction measurement unit 20 on the fundus Ef (central fixation).

(S2: Perform Objective Refraction Measurement)

Next, the controller 70 controls the refraction measurement unit 20 to perform objective refraction measurement with the fixation target projected on the measurement optical axis of the optical system of the refraction measurement unit 20. Thereby, the light is projected onto the fundus Ef of the subject's eye E, and the dioptric power in the central region including the fovea of the subject's eye E can be obtained by analyzing the ring pattern image formed by the reflected light of the light projected onto the fundus Ef of the subject's eye E.

(S3: Perform OCT Measurement)

Subsequently, the controller 70 controls the OCT unit 30 to perform OCT measurement (OCT scan) with the fixation target projected on the measurement optical axis of the optical system of the refraction measurement unit 20 (OCT unit 30). In step S3, the radial scan centered on the central region is performed, for example. Thereby, the B-scan image (OCT data) of the central region including the fovea of the fundus Ef can be acquired. Further, the B-scan image can be acquired along the tangential plane and the sagittal plane.

(S4: Perform Segmentation Processing)

Next, the analyzer 61 specifies the predetermined layer region by performing segmentation processing on the B-scan image acquired in step S3, and acquires a Hight data [pixel] of the layer region in the B-scan image. For example, the predetermined layer region is the OS-RPE boundary surface. The Height data corresponds to a distance in the depth direction from a predetermined reference position in the B-scan image.

(S5: Construct Eyeball Model)

The analyzer 61 acquired a distance [mm] of the Height data using a pixel spacing correction value [mm/pixel]. The pixel spacing correction value is defined by the optical system and is specific to the apparatus.

Further, the eyeball model construction unit 62 constructs the eyeball model using the obtained Height data as the fundus shape data.

Figure 3:
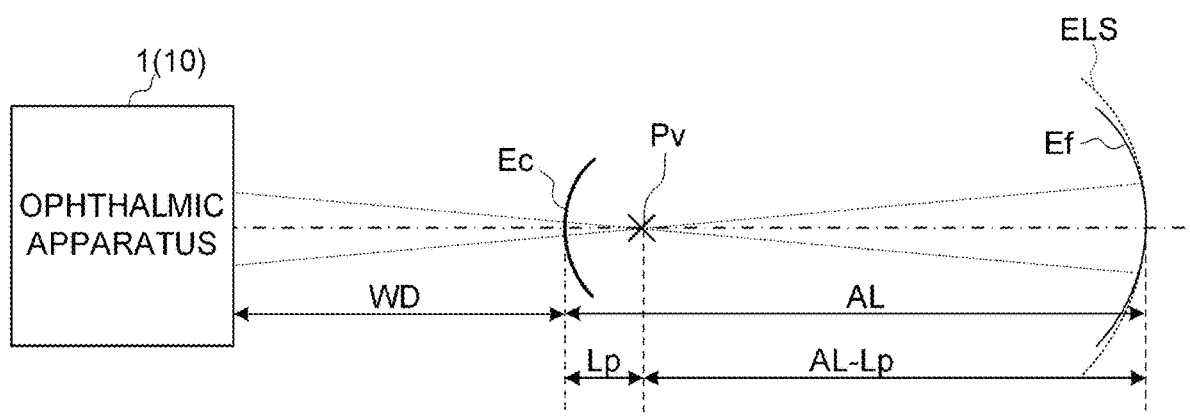
FIG. 3 is a schematic diagram for explaining the operation of the ophthalmic apparatus according to the first embodiment.

FIG. 3 shows a diagram explaining the operation of the eyeball model construction unit 62 according to the embodiments. FIG. 3 schematically illustrates a part of parameters of the eyeball model.

The eyeball model construction unit 62 constructs the eyeball model having a predetermined corneal curvature radius (for example, 7.7 mm) and a predetermined axial length (for example, 24.2 mm), using the parameter(s) of an eyeball model such as Gullstrand schematic eye.

The eyeball model construction unit 62 sets a pivot point Pv between the cornea Ec and the fundus Ef in the eyeball model, as shown in FIG. 3. The pivot point Pv is specific to the apparatus. Typically, a position corresponding to a pupil position disposed at a position optically conjugate with the galvano mirror included in the scan system is set as the pivot point Pv. The pivot point Pv is a position of 3 mm posterior to the cornea Ec, for example. Equidistant (equal optical path length) positions (ELS) centered on the pivot point Pv correspond to flat positions in the B-scan image obtained by performing OCT measurement.

In the eyeball model, the axial length AL and the distance Lp from the anterior surface (posterior surface) of the cornea to the pivot point Pv are known. Therefore, the distance (AL–Lp) from the pivot point Pv to the fundus Ef is known.

When the curvature radius of the fundus Ef is equal to the distance (AL–Lp), the equidistant positions correspond to the flat positions in the B scan image as described above. Thereby, the analyzer 61 (or eyeball model construction unit 62) can specify the shape (for example, curvature radius) of the fundus Ef from the distance [mm] of the obtained Height data.

Therefore, the analyzer 61 (or eyeball model construction unit 62) obtains the difference (fundus shape difference data) Δh [mm] of the height of the peripheral region relative to the central region (fovea). The difference Δh may be obtained for each A-line in the B-scan image, or may be obtained by fitting with an arbitrary function such as a polynomial or an aspheric expression (polynomial including a conic constant).

(S6: Calculate Dioptric Power in Peripheral Region)

Next, the calculator 63 calculates the dioptric power in the peripheral region.

First, the calculator 63 defines a refractive power of the whole eye system in order to relate the shape of the fundus and the dioptric power. In a typical eyeball model, the refractive power of the whole eye system is 58.64 [Diopter]. Examples of the eyeball model include a Gullstrand schematic eye (precise schematic eye, accommodation pausing state). In the air conversion length, the focal length of the whole eye system is "1000/58.64=17.05" [mm]. Information on unit [mm] obtained using the pixel spacing correction value usually represents the distance in tissue of the living body. Thereby, the focal length of the whole eye system in tissue of the living body can be calculated by multiplying a refractive index. Assuming that the equivalent refractive index of the whole eye system is n=1.38, the focal length ft of the whole eye system in tissue of the living body is "1000/58.64×1.38=23.53" [mm].

The calculator 63 calculates the difference ΔD of the eyeball refractive power at the position of the difference Δh of the height of the peripheral region with respect to the central region (fovea) according to equation (1). The difference ΔD corresponds to the difference in the eyeball refractive power relative to the central region including the fovea.

[Equation 1]

$$\Delta D = \frac{1000}{23.53 - \Delta h} - \frac{1000}{23.53} \quad (1)$$

For example, when Δh=0.1 [mm] (in tissue), ΔD=0.18 [Diopter].

The calculator 63 obtains the dioptric power SEp in the peripheral region by applying the difference ΔD of equation (1) to the equivalent spherical power SE in the central region, as shown in equation (2).

[Equation 2]

$$SEp = SE + \Delta D \quad (2)$$

The calculator 63 may obtain the dioptric power in the peripheral region in the B-scan image for each A-line, or may obtain by fitting with an arbitrary function.

This terminates the operation of the ophthalmic apparatus 1 (END).

Second Embodiment

In the same way as the first embodiment, the ophthalmic apparatus according to the second embodiment calculates (i.e., estimates) a dioptric power in a peripheral region outside a central region on the fundus from the dioptric power in the central region including the fovea in the fundus of the subject's eye and the shape of the fundus. The difference between the ophthalmic apparatus according to the second embodiment and the ophthalmic apparatus 1 according to the first embodiment is the point of calculating the dioptric power in the peripheral region using axial length data (measurement value of the axial length) of the subject's eye E. Hereinafter, the ophthalmic apparatus according to the second embodiment will be described mainly about the differences from the first embodiment.

The configuration of the ophthalmic apparatus according to the second embodiment is similar to the configuration of the ophthalmic apparatus 1 according to the first embodiment. Thus, the description of the configuration of the ophthalmic apparatus according to the present embodiment will be omitted.

Operation Example

The operation of the ophthalmic apparatus according to the second embodiment will be described.

Figure 4:
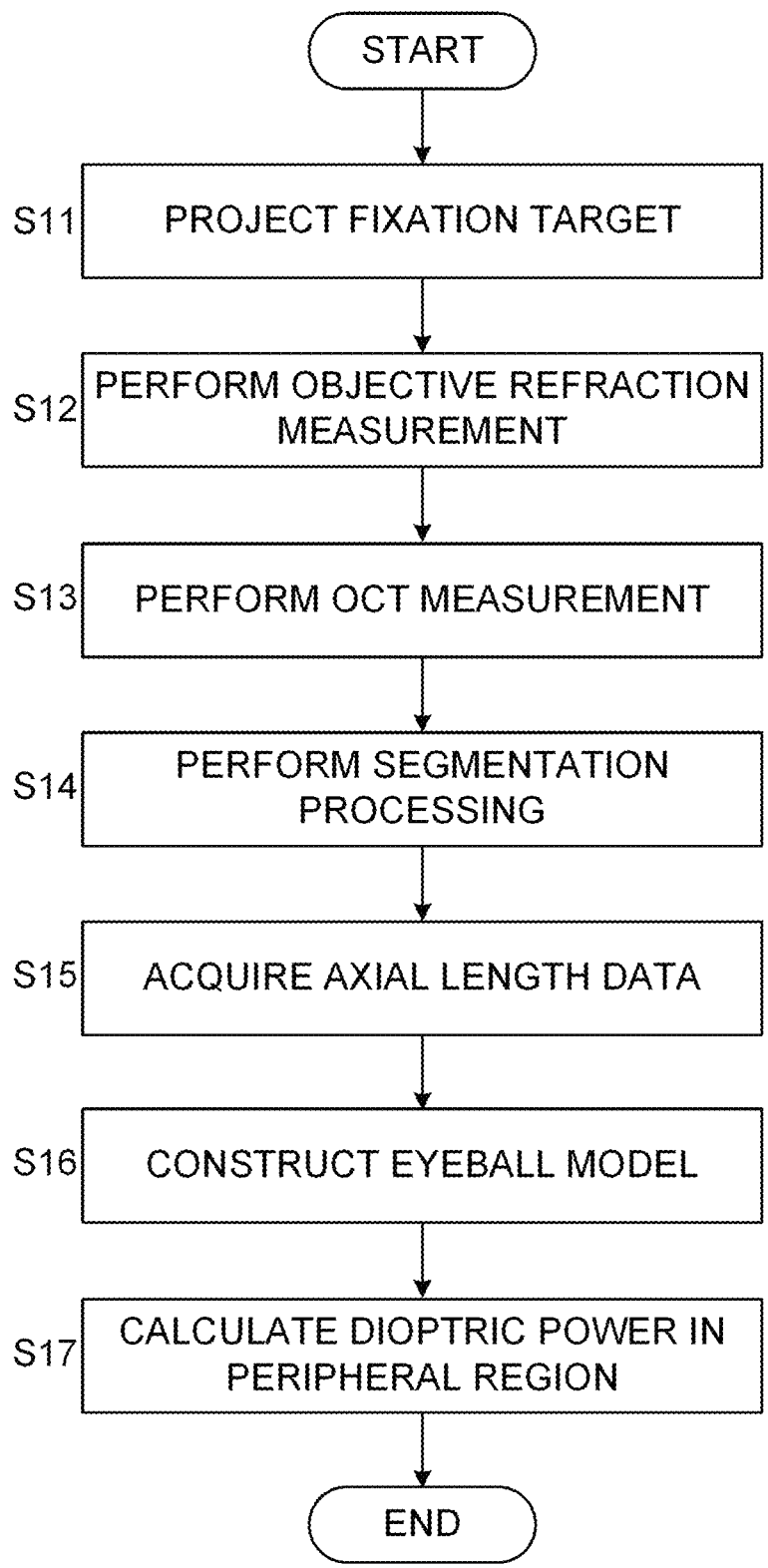
FIG. 4 is a flow chart illustrating an example of an operation of the ophthalmic apparatus according to a second embodiment.

FIG. 4 shows an example of the operation of the ophthalmic apparatus according to the second embodiment. FIG. 4 represents a flowchart of an example of the operation of the ophthalmic apparatus. The storage unit in the controller 70 stores the computer program for realizing the processing shown in FIG. 4. The controller 70 operates according to the computer program, and thereby the controller 70 executes the processing shown in FIG. 4.

(S11: Project Fixation Target)

First, in the same way as in step S1, the controller 70 controls the fixation projection system (not shown) to project the fixation target on the measurement optical axis of the optical system of the refraction measurement unit 20 (central fixation).

(S12: Perform Objective Refraction Measurement)

Next, in the same way as in step S2, the controller 70 controls the refraction measurement unit 20 to perform objective refraction measurement with the fixation target projected on the measurement optical axis of the optical system of the refraction measurement unit 20 on the fundus Ef.

(S13: Perform OCT Measurement)

Subsequently, in the same way as in step S3, the controller 70 controls the OCT unit 30 to perform OCT measurement (OCT scan) with the fixation target projected on the measurement optical axis of the optical system of the refraction measurement unit 20 (OCT unit 30).

(S14: Perform Segmentation Processing)

Next, in the same way as in step S4, the analyzer 61 specifies the predetermined layer region by performing segmentation processing on the B-scan image acquired in step S13, and acquires the Hight data [pixel] of the layer region in the B-scan image. For example, the predetermined layer region is the OS-RPE boundary surface.

(S15: Acquire Axial Length Data)

Next, the analyzer 61 acquires the axial length data of the subject's eye E. The axial length data includes a measurement value of the axial length of the subject's eye E. For example, the analyzer 61 obtains the axial length by analyzing the OCT data. The OCT data is acquired by performing OCT measurement in step S13. In some embodiments, the analyzer 61 acquires the axial length data from the electronic health record system. In some embodiments, the analyzer 61 acquires the axial length data from the external axial length measurement apparatus.

(S16: Construct Eyeball Model)

In the same way as in step S5, the analyzer 61 acquired the distance [mm] of the Height data using the pixel spacing correction value [mm/pixel].

Further, in the same way as in step S5, the eyeball model construction unit 62 constructs the eyeball model using the obtained Height data as the fundus shape data. The eyeball model construction unit 62 constructs a new eyeball model by replacing the axial length, the axial length being one of the parameters of the schematic eye such as Gullstrand schematic eye, with the axial length acquired in step S15. In the same way as in step S5, the eyeball model construction unit 62 obtains the difference (fundus shape difference data) $\Delta h$ [mm] of the height of the peripheral region relative to the central region (fovea), using the constructed new eyeball model.

(S17: Calculate Dioptric Power in Peripheral Region)

Next, in the same way as in step S6, the calculator 63 obtains the difference $\Delta D$ of the eyeball refractive power using the obtained difference $\Delta h$, and calculates the dioptric power in the peripheral region using the obtained difference $\Delta D$.

This terminates the operation of the ophthalmic apparatus according to the second embodiment (END).

Third Embodiment

In the same way as the first embodiment, the ophthalmic apparatus according to the third embodiment calculates a dioptric power in a peripheral region outside a central region on the fundus from the dioptric power in the central region including the fovea in the fundus of the subject's eye and the shape of the fundus. The difference between the ophthalmic apparatus according to the third embodiment and the ophthalmic apparatus 1 according to the first embodiment is the point of calculating the dioptric power in the peripheral region using corneal shape data (measurement value of the corneal shape) of the subject's eye E. Hereinafter, the ophthalmic apparatus according to the third embodiment will be described mainly about the differences from the first embodiment.

The configuration of the ophthalmic apparatus according to the third embodiment is similar to the configuration of the ophthalmic apparatus 1 according to the first embodiment. Thus, the description of the configuration of the ophthalmic apparatus according to the present embodiment will be omitted.

Operation Example

The operation of the ophthalmic apparatus according to the third embodiment will be described.

Figure 5:
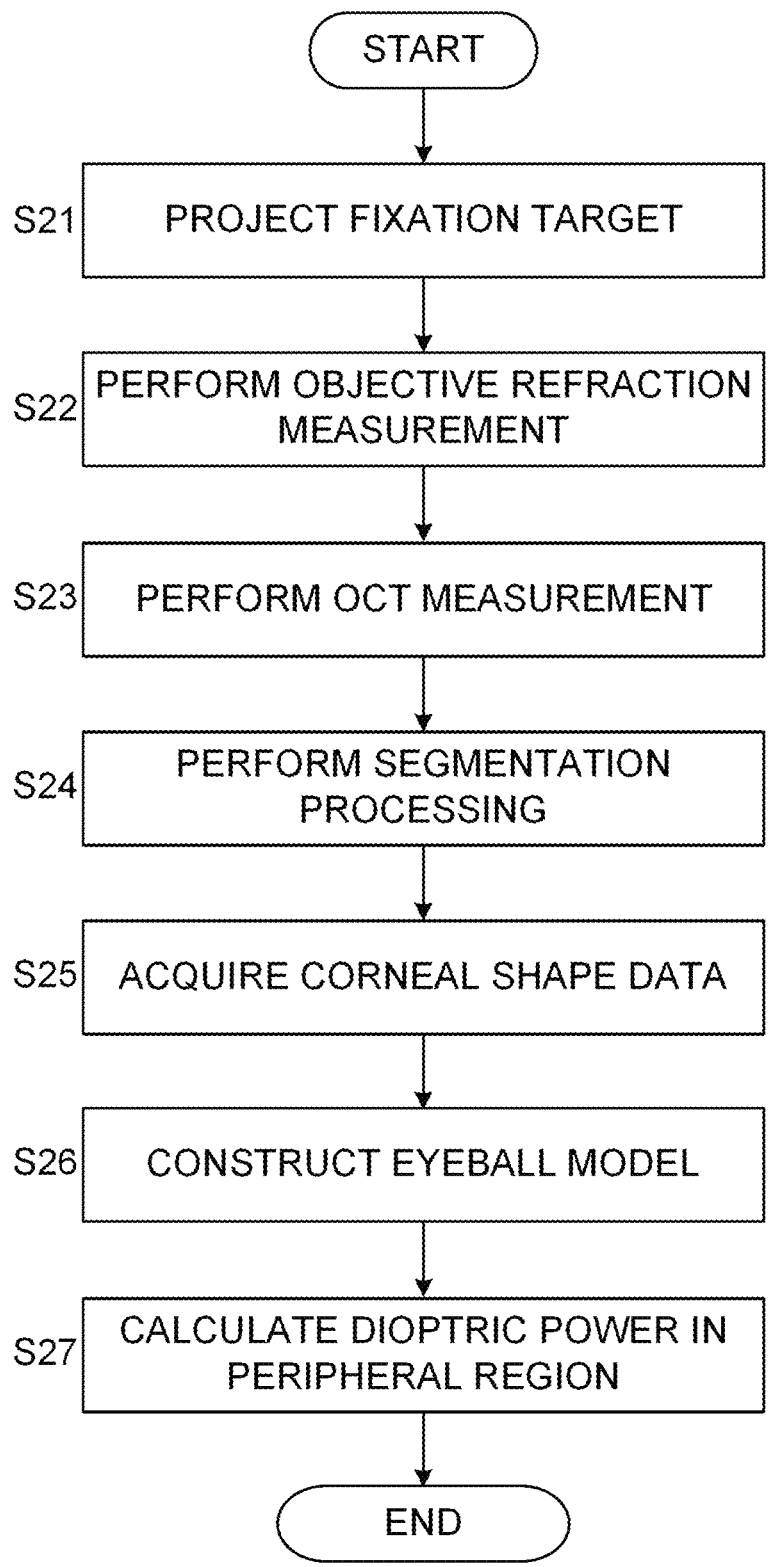
FIG. 5 is a flow chart illustrating an example of an operation of the ophthalmic apparatus according to a third embodiment.

FIG. 5 shows an example of the operation of the ophthalmic apparatus according to the third embodiment. FIG. 5 represents a flowchart of an example of the operation of the ophthalmic apparatus. The storage unit in the controller 70 stores the computer program for realizing the processing shown in FIG. 5. The controller 70 operates according to the computer program, and thereby the controller 70 executes the processing shown in FIG. 5.

(S21: Project Fixation Target)

First, in the same way as in step S1, the controller 70 controls the fixation projection system (not shown) to project the fixation target on the measurement optical axis of the optical system of the refraction measurement unit 20 (central fixation).

(S22: Perform Objective Refraction Measurement)

Next, in the same way as in step S2, the controller 70 controls the refraction measurement unit 20 to perform objective refraction measurement with the fixation target projected on the measurement optical axis of the optical system of the refraction measurement unit 20 on the fundus Ef.

(S23: Perform OCT Measurement)

Subsequently, in the same way as in step S3, the controller 70 controls the OCT unit 30 to perform OCT measurement (OCT scan) with the fixation target projected on the measurement optical axis of the optical system of the refraction measurement unit 20 (OCT unit 30).

(S24: Perform Segmentation Processing)

Next, in the same way as in step S4, the analyzer 61 specifies the predetermined layer region by performing segmentation processing on the B-scan image acquired in step S23, and acquires the Hight data [pixel] of the layer region in the B-scan image. For example, the predetermined layer region is the OS-RPE boundary surface.

(S25: Acquire Corneal Shape Data)

Next, the analyzer 61 acquires corneal shape data of the subject's eye E. The corneal shape data includes a measurement value of the shape of the cornea Ec of the subject's eye E. Examples of the shape of the cornea include a corneal curvature radius and a corneal thickness. For example, the analyzer 61 acquires the corneal shape data including the corneal curvature radius, the thickness includes, or the like from the electronic health record system. In some embodiments, the analyzer 61 acquires the corneal shape data from an external cornea shape measurement apparatus. In some embodiments, the analyzer 61 acquires the corneal thickness by analyzing the OCT data. The OCT data is acquired by performing OCT measurement in step S23.

(S26: Construct Eyeball Model)

In the same way as in step S5, the analyzer 61 acquired the distance [mm] of the Height data using the pixel spacing correction value [mm/pixel].

Further, in the same way as in step S5, the eyeball model construction unit 62 constructs the eyeball model using the obtained Height data as the fundus shape data. The eyeball model construction unit 62 constructs a new eyeball model by replacing the parameter representing the corneal shape, the parameter being one of the parameters of the schematic eye such as Gullstrand schematic eye, with the corneal shape data acquired in step S25. In the same way as in step S5, the eyeball model construction unit 62 obtains the difference Δh [mm] of the height of the peripheral region relative to the central region (fovea), using the constructed new eyeball model.

(S27: Calculate Dioptric Power in Peripheral Region)

Next, in the same way as in step S6, the calculator 63 obtains the difference ΔD of the eyeball refractive power using the obtained difference Δh, and calculates the dioptric power in the peripheral region using the obtained difference ΔD.

This terminates the operation of the ophthalmic apparatus according to the third embodiment (END).

Fourth Embodiment

In the same way as the first embodiment, the ophthalmic apparatus according to the fourth embodiment calculates (i.e., estimates) a dioptric power in a peripheral region outside a central region on the fundus from the dioptric power in the central region including the fovea in the fundus of the subject's eye and the shape of the fundus. The difference between the ophthalmic apparatus according to the fourth embodiment and the ophthalmic apparatus 1 according to the first embodiment is the point of constructing the eyeball model using a plurality of actual measurement values of the subject's eye E and performing ray tracing processing to calculate the dioptric power in the peripheral region. Examples of the actual measurement value include a measured value of the axial length, a measured value of the corneal shape, a measured value of the anterior chamber depth, a measured value of the curvature of the crystalline lens, and a measured value of the thickness of the crystalline lens. Hereinafter, the ophthalmic apparatus according to the fourth embodiment will be described mainly about the differences from the first embodiment.

The configuration of the ophthalmic apparatus according to the fourth embodiment is similar to the configuration of the ophthalmic apparatus according to the first embodiment. Thus, the description of the configuration of the ophthalmic apparatus according to the present embodiment will be omitted.

Operation Example

The operation of the ophthalmic apparatus according to the fourth embodiment will be described.

Figure 6:
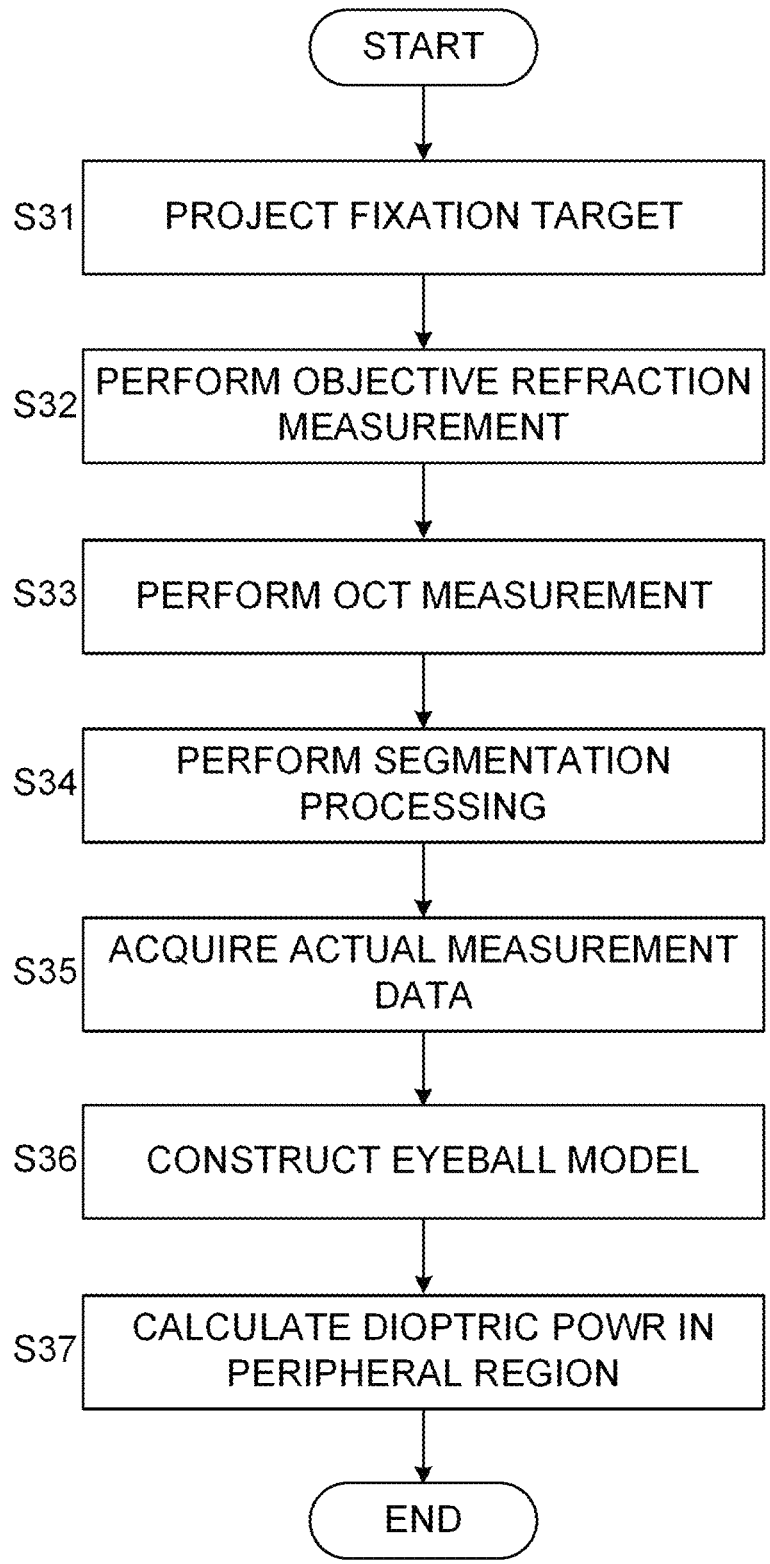
FIG. 6 is a flow chart illustrating an example of an operation of the ophthalmic apparatus according to a fourth embodiment.

FIG. 6 shows an example of the operation of the ophthalmic apparatus according to the fourth embodiment. FIG. 6 represents a flowchart of an example of the operation of the ophthalmic apparatus. The storage unit in the controller 70 stores the computer program for realizing the processing shown in FIG. 6. The controller 70 operates according to the computer program, and thereby the controller 70 executes the processing shown in FIG. 6.

(S31: Project Fixation Target)

First, in the same way as in step S1, the controller 70 controls the fixation projection system (not shown) to project the fixation target on the measurement optical axis of the optical system of the refraction measurement unit 20 (central fixation).

(S32: Perform Objective Refraction Measurement)

Next, in the same way as in step S2, the controller 70 controls the refraction measurement unit 20 to perform objective refraction measurement with the fixation target projected on the measurement optical axis of the optical system of the refraction measurement unit 20 on the fundus Ef.

(S33: Perform OCT Measurement)

Subsequently, in the same way as in step S3, the controller 70 controls the OCT unit 30 to perform OCT measurement (OCT scan) with the fixation target projected on the measurement optical axis of the optical system of the refraction measurement unit 20 (OCT unit 30).

(S34: Perform Segmentation Processing)

Next, in the same way as in step S4, the analyzer 61 specifies the predetermined layer region by performing segmentation processing on the B-scan image acquired in step S33, and acquires the Hight data [pixel] of the layer region in the B-scan image. For example, the predetermined layer region is the OS-RPE boundary surface.

(S35: Acquire Actual Measurement Data)

Next, the analyzer 61 acquires actual measurement data of the subject's eye E. The actual measurement data includes a measurement value of the axial length of the subject's eye E, a measurement value of the corneal shape of the subject's eye E, a measured value of the anterior chamber depth of the subject's eye E, a measured value of the curvature of the crystalline lens of the subject's eye E, and a measured value of the thickness of the crystalline lens of the subject's eye E. Examples of the corneal shape include a corneal curvature radius and a corneal thickness. For example, the analyzer 61 obtains the axial length, the corneal thickness, the anterior chamber depth, and the thickness of the crystalline lens by analyzing the OCT data. The OCT data is acquired by performing OCT measurement in step S33. For example, the analyzer 61 acquires the corneal shape data including the corneal curvature radius, etc. from the electronic health record system. In some embodiments, the analyzer 61 acquires the actual measurement data from the electronic health record system. In some embodiments, the analyzer 61 acquires the actual measurement data from one or more external measurement apparatuses. In some embodiments, the analyzer 61 acquires the corneal shape data from an external cornea shape measurement apparatus.

(S36: Construct Eyeball Model)

In the same way as in step S5, the analyzer 61 acquired the distance [mm] of the Height data using the pixel spacing correction value [mm/pixel].

Further, in the same way as in step S5, the eyeball model construction unit 62 constructs the eyeball model using the obtained Height data as the fundus shape data. The eyeball model construction unit 62 constructs a new eyeball model by replacing at least one of the parameters of the schematic eye such as Gullstrand schematic eye with the actual measurement data acquired in step S35.

(S37: Calculate dioptric power in peripheral region)

The calculator 63 (or the data processor 60) performs ray tracing processing on rays using the constructed new eyeball model (for example, pupil diameter=φ4), the rays entering from the cornea Ec, passing through the pupil, and reaching the fundus Ef. In the ray tracing processing, a position of the object point is set to a position corresponding to a far point. The far point is obtained from the dioptric power (equivalent spherical power SE) in the central region acquired in step S32. The far distance L from the cornea Ec to the position corresponding to the far point is "−1000/SE" [mm].

First, calculator 63 performs the ray tracing processing for the central region. The measured data is applied to the eyeball model as described above. Thus, even in the central region, the ray may not converge at the fundus Ef. In this case, the calculator 63 finely adjusts the parameter(s) of the eyeball model so that the ray converges in the central region (i.e., so that the surface of the fundus Ef is the best image surface).

Next, calculator 63 performs the ray tracing processing for the peripheral region using the eyeball model with the parameters finely adjusted. That is, the rays having incident angles with respect to the measurement optical axis passing through a center of rotation of the eye are traced. The calculator 63 obtains the distance to the object point such that the rays converge on the fundus Ef in the peripheral region, by performing ray tracing processing while changing the distance to the object point. The obtained distance to the object point corresponds to the far point distance Lp in the peripheral region. The calculator 63 can obtain the dioptric power SEp [Diopter] in the peripheral region using equation (3).

[Equation 3]

$$SEp = -\frac{1000}{Lp} \quad (3)$$

The calculator 63 performs ray tracing processing while changing the incident angle in a predetermined incident angle range, and obtains the dioptric power SEp in the peripheral region for each incident angle (angle of view). The dioptric power in the peripheral region may be a discrete value for each incident angle or may be fitted with an arbitrary function in the incident angle range.

This terminates the operation of the ophthalmic apparatus according to the fourth embodiment (END).

In the fourth embodiment, the eyeball model is finely adjusted so that the rays converge at the fundus Ef in the central region. Thus, the obtained dioptric power in the peripheral region corresponds to obtaining a relative dioptric power for the central region.

Fifth Embodiment

The ophthalmic apparatus according to the fifth embodiment specifies a shape of the central region including the fovea on the fundus of the subject's eye, and obtains a dioptric power reflecting the specified shape. In the fifth embodiment, a tilt angle of a predetermined layer region of the fundus with respect to the horizontal direction (a predetermined reference direction) may be specified as the shape of the central region of the fundus. Example of the predetermined layer region include the OS-RPE boundary surface. Hereinafter, the ophthalmic apparatus according to the fifth embodiment will be described mainly about the differences from the first embodiment.

The configuration of the ophthalmic apparatus according to the fifth embodiment is the same as the configuration of the ophthalmic apparatus 1 according to the first embodiment except that the eyeball model construction unit 62 is omitted. Thus, the explanation for the configuration of the ophthalmic apparatus according to the present embodiment is omitted.

Operation Example

The operation of the ophthalmic apparatus according to the fifth embodiment will be described.

Figure 7:
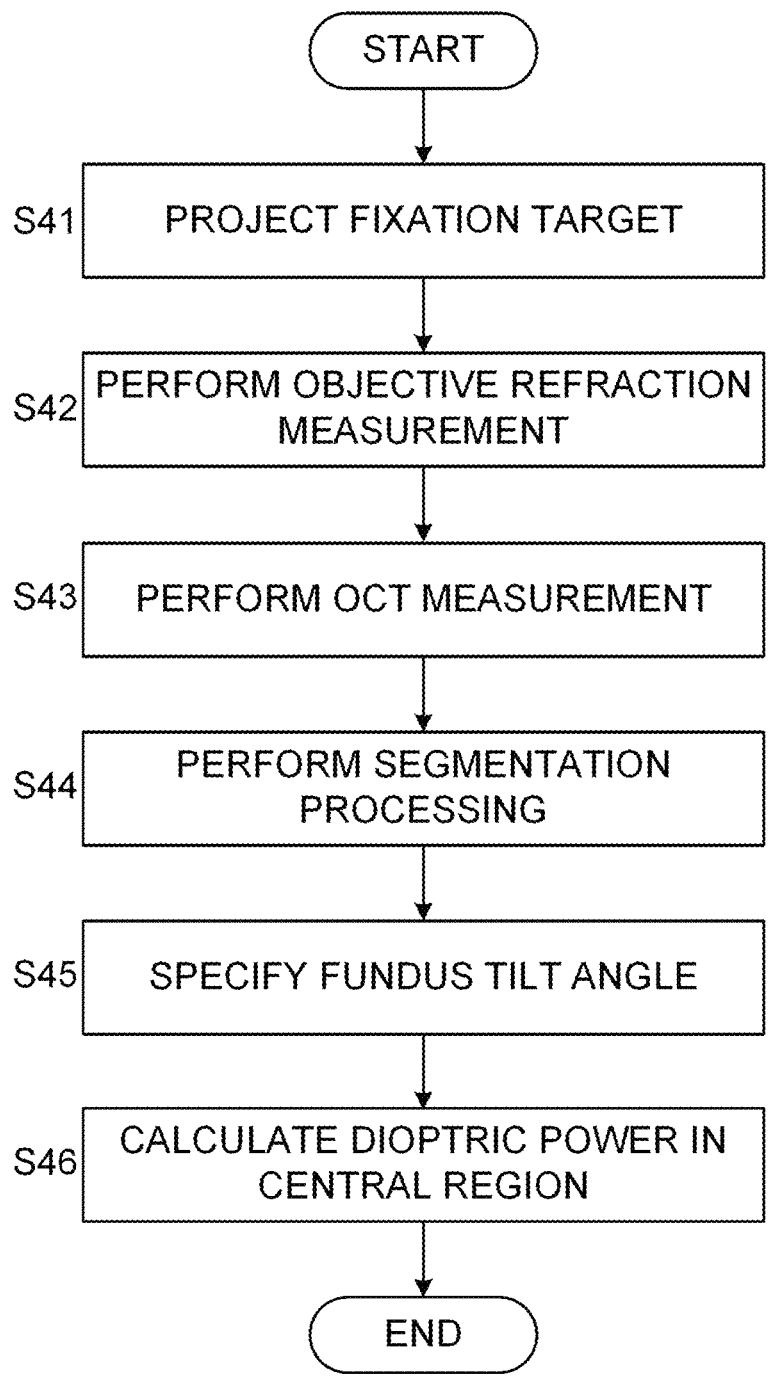
FIG. 7 is a flow chart illustrating an example of an operation of the ophthalmic apparatus according to a fifth embodiment.

FIG. 7 shows an example of the operation of the ophthalmic apparatus according to the fifth embodiment. FIG. 7 represents a flowchart of an example of the operation of the ophthalmic apparatus. The storage unit in the controller 70 stores the computer program for realizing the processing shown in FIG. 7. The controller 70 operates according to the computer program, and thereby the controller 70 executes the processing shown in FIG. 7.

(S41: Project Fixation Target)

First, in the same way as in step S1, the controller 70 controls the fixation projection system (not shown) to project the fixation target on the measurement optical axis of the optical system of the refraction measurement unit 20 (central fixation).

(S42: Perform Objective Refraction Measurement)

Next, in the same way as in step S2, the controller 70 controls the refraction measurement unit 20 to perform objective refraction measurement with the fixation target projected on the measurement optical axis of the optical system of the refraction measurement unit 20 on the fundus Ef. Thereby, the ring pattern image is acquired.

(S43: Perform OCT Measurement)

Subsequently, in the same way as in step S3, the controller 70 controls the OCT unit 30 to perform OCT measurement (OCT scan) with the fixation target projected on the measurement optical axis of the optical system of the refraction measurement unit 20 (OCT unit 30). In step S43, the cross scan in the horizontal direction and the vertical direction is performed, for example. That is, the first scan in the horizontal direction and the second scan in the vertical direction intersecting the first scan are performed or the cross radial scan in the horizontal direction and the vertical direction is performed. Alternatively, in step S43, the radial scan centered on the central region may be performed, for example. Thereby, the B-scan images can be acquired along the tangential plane and the sagittal plane.

(S44: Perform Segmentation Processing)

Next, the analyzer 61 specifies a predetermined layer region by performing segmentation processing in the same way as in step S4 and acquires a Hight data [pixel] of the layer region in the B-scan image, for each of the horizontal and vertical B-scan images acquired in step S43. For example, the predetermined layer region is the OS-RPE boundary surface.

(S45: Specify Fundus Tilt Angle)

Next, in the same way as in step S5, the analyzer 61 acquired the distance [mm] of the Height data using the pixel spacing correction value [mm/pixel].

The analyzer 61 calculates a tilt angle θh of the fundus plane for the B-scan image in the horizontal direction and a tilt angle θv of the fundus plane for the B-scan image in the vertical direction, using the obtained Height data.

The tilt angles θh and θv can be calculated using the same method as for the tilt angle g1, as follows.

Figure 8:
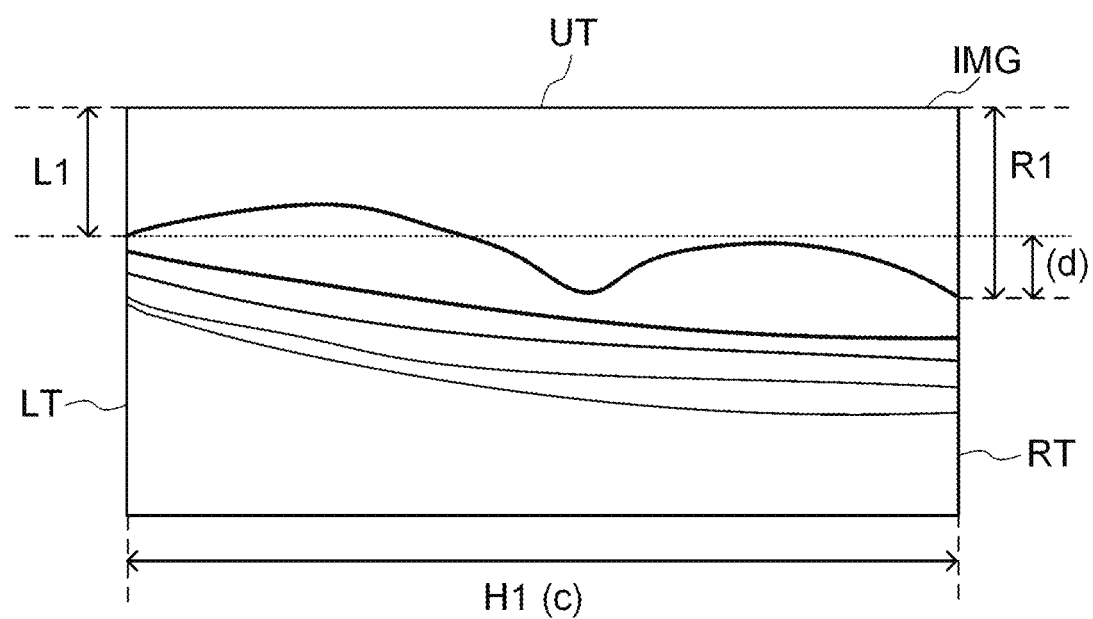
FIG. 8 is a schematic diagram for explaining the operation of the ophthalmic apparatus according to the fifth embodiment.

FIG. 8 schematically shows the B-scan image in the horizontal direction.

In FIG. 8, at the left end LT of the frame of B-scan image IMG, the distance in the vertical direction from the upper end UT of the frame to the image region of the site corresponding to the predetermined layer region in the fundus Ef is set as L1. Examples of the predetermined layer region include the OS-RPE boundary surface and the nerve fiber layer. In the same manner, at the right end RT of the frame of the B-scan image IMG, the distance in the vertical direction from the upper end UT of the frame to the image region of the site corresponding to the layer region is set as R1. The distance L1 is obtained using the Height data at the left end LT of the frame. The distance R1 is obtained using the Height data at the right end RT of the frame. The analyzer 61 obtains a value d corresponding to the actual dimension for the difference (|R1−L1|) in the vertical direction of the image region of the site at the left end LT of the frame and the right end RT of the frame in B-scan image IMG.

Next, the analyzer 61 obtains a value "c" corresponding to the actual dimension for the distance H1 in the horizontal direction of the frame of the B-scan image IMG corresponding to the OCT measurement range. For example, the value "c" is specified using the pixel spacing correction value [mm/pixel] for the length of scanning range in the horizontal direction.

The analyzer 61 obtains an inclination angle g0 [degree] according to equation (4).

[Equation 4]

$$g0 = \arctan\left(\frac{|d|}{c}\right) \quad (4)$$

In some embodiments, the analyzer 61 obtains the tilt angle of the fundus plane by correcting the inclination angle g0 according to a misalignment amount between the measurement optical axis and the eyeball optical axis.

(In the Case that the Measurement Optical Axis and the Eyeball Optical Axis Substantially Coincide with Each Other)

When the measurement optical axis and the eyeball optical axis (visual axis) substantially coincide with each other, the analyzer 61 outputs the inclination angle g0 of the B-scan image as the tilt angle g1 of the fundus plane, without correcting the inclination angle g0 as shown in equation (5).

[Equation 5]

$$g1 = g0 = \arctan\left(\frac{|d|}{c}\right) \quad (5)$$

(In the Case that the Eyeball Optical Axis is Shifted with Respect to the Measurement Optical Axis)

When the eyeball optical axis is shifted with respect to the measurement optical axis, the analyzer 61 obtains the tilt angle g1 of the fundus plane by correcting the inclination angle g0 of the B-scan image based on a shift amount.

For example, the analyzer 61 obtains a correction angle φ1 according to a linear expression with the shift amount ds as variable shown in equation (6), and then obtains the tilt angle g1 of the fundus plane by correcting the inclination angle g0 using the obtained correction angle φ1 as shown in equation (7). In equation (6), α1 and c1 are constants. For example, α1 and c1 can be obtained using the schematic eye data.

[Equation 6]

$$\varphi1 = \alpha1 \times ds + c1 \quad (6)$$

[Equation 7]

$$g1 = g0 - \varphi1 \quad (7)$$

(In the Case that the Eyeball Optical Axis is Tilted with Respect to the Measurement Optical Axis)

When the eyeball optical axis is tilted with respect to the measurement optical axis, the analyzer 61 obtains the tilt angle g1 of the fundus plane by correcting the inclination angle g0 of the B-scan image based on a tilt amount.

For example, the analyzer 61 obtains a correction angle φ2 according to a linear expression with the tilt amount dt as variable shown in equation (8), and then obtains the tilt angle g1 of the fundus plane by correcting the inclination angle g0 using the obtained correction angle φ2 as shown in equation (9). In equation (8), α2 and c2 are constants. For example, α2 and c2 can be obtained using the schematic eye data.

[Equation 8]

$$\varphi2 = \alpha2 \times dt + c2 \quad (8)$$

[Equation 9]

$$g1 = g0 - \varphi2 \quad (9)$$

(In the Case that the Eyeball Optical Axis is Shifted and Tilted with Respect to the Measurement Optical Axis)

When the eyeball optical axis is shifted and tilted with respect to the measurement optical axis, the analyzer 61 obtains the tilt angle g1 of the fundus plane by correcting the inclination angle g0 of the B-scan image based on the shift amount and the tilt amount.

For example, in a range with the small shift amount ds and the small tilt amount dt, the analyzer 61 obtains a correction angle φ3 according to an equation with the shift amount ds and the tilt amount dt as variables shown in equation (10), and then obtains the tilt angle g1 of the fundus plane by correcting the inclination angle g0 using the obtained correction angle φ3 as shown in equation (11). In some embodiments, equation (10) is a combining equation obtained by linearly combined an equation for obtaining the correction angle of the shift amount and an equation for obtaining the correction angle of the tilt amount. In equation (10), α3, α4 and c3 are constants. For example, α3, α4, and c3 can be obtained using the schematic eye data.

[Equation 10]

$$\varphi 3 = \alpha 3 \times ds + \alpha 4 \times dt + c3 \quad (10)$$

[Equation 11]

$$g1 = g0 - \varphi 3 \quad (11)$$

(S46: Calculate Dioptric Power in Central Region)

Next, for the horizontal and vertical directions respectively, the calculator 63 corrects the ring pattern image obtained in step S42 in accordance with the tilt angles θh and θv of the fundus plane specified in step S45. The calculator 63 performs ellipse approximation on the corrected ring pattern image, and obtains the dioptric power using the obtained elliptical shape by a known method. The obtained dioptric power is calculated as the dioptric power in the central region.

For example, a major axis of the ring pattern image is LA, and a minor axis of the ring pattern image is LB, the ring pattern image being acquired when the tilt angle of the fundus plane is 0 degrees. When the fundus plane is tilted in the major axis direction and the tilt angle is θ degree, the major axis of the ellipse approximated from the acquired ring pattern image is "LA/cos θ", and the minor axis is LB. Therefore, the calculator 63 can correct the ring pattern image by multiplying cos θ in the major axis direction of the ellipse obtained by approximating the ring pattern image acquired in step S42. The same applies to the case of tilting in the minor axis direction. For example, the calculator 63 can correct the ring pattern image by obtaining the tilt angle in the major axis direction of the ellipse and the tilt angle in the minor axis direction of the ellipse from each of the tilt angles in the horizontal and vertical directions.

This terminates the operation of the ophthalmic apparatus according to the fifth embodiment (END).

Sixth Embodiment

The ophthalmic apparatus according to the sixth embodiment specifies a shape of the peripheral region outside the central region including the fovea on the fundus of the subject's eye, and obtains a dioptric power reflecting the specified shape. In the sixth embodiment, in the same way as in the fifth embodiment, a tilt angle of a predetermined layer region of the fundus with respect to the horizontal direction (a predetermined reference direction) is specified as the shape of the peripheral region of the fundus. Example of the predetermined layer region include the OS-RPE boundary surface. Hereinafter, the ophthalmic apparatus according to the sixth embodiment will be described mainly about the differences from the fifth embodiment.

The configuration of the ophthalmic apparatus according to the sixth embodiment is similar to the configuration of the ophthalmic apparatus according to the fifth embodiment. Thus, the description of the configuration of the ophthalmic apparatus according to the present embodiment will be omitted.

Operation Example

The operation of the ophthalmic apparatus according to the sixth embodiment will be described.

Figure 9:
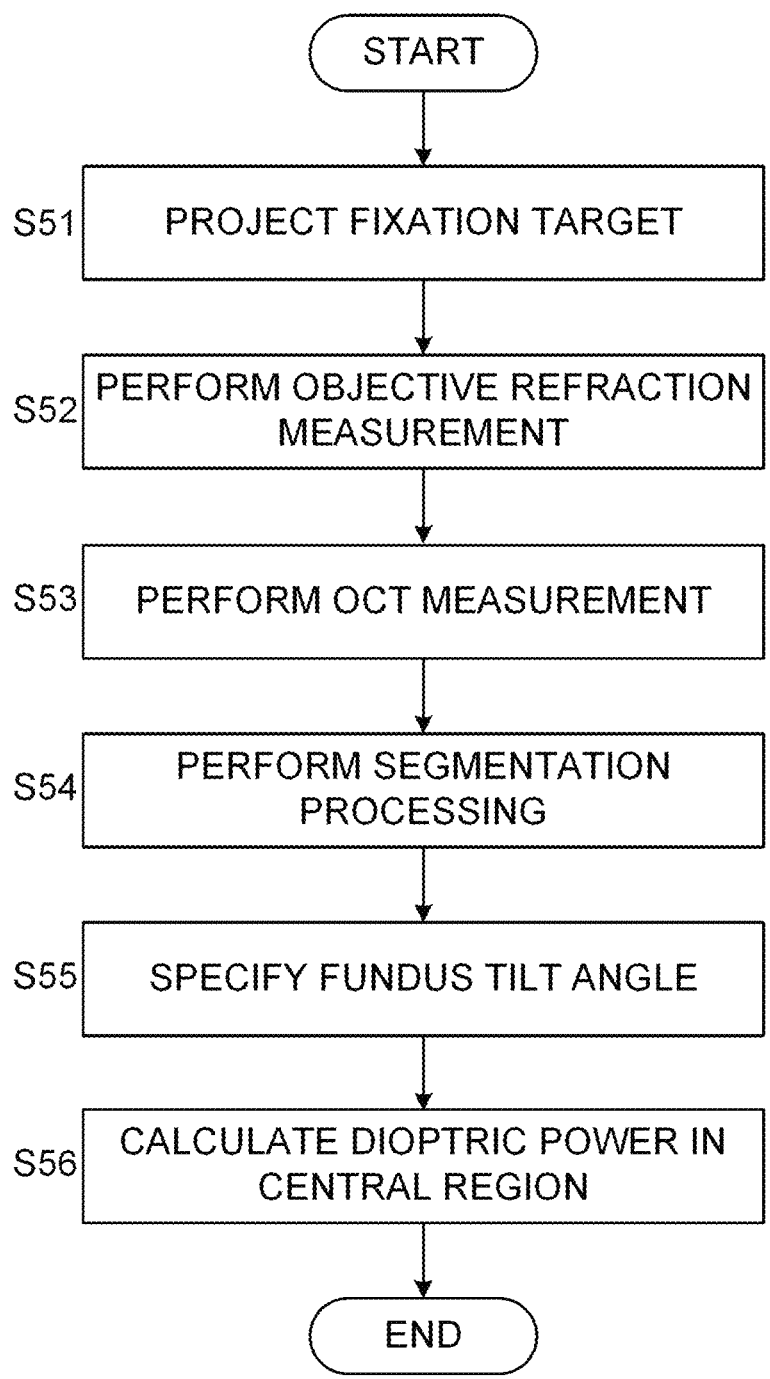
FIG. 9 is a flow chart illustrating an example of an operation of the ophthalmic apparatus according to a sixth embodiment.

FIG. 9 shows an example of the operation of the ophthalmic apparatus according to the sixth embodiment. FIG. 9 represents a flowchart of an example of the operation of the ophthalmic apparatus. The storage unit in the controller 70 stores the computer program for realizing the processing shown in FIG. 9. The controller 70 operates according to the computer program, and thereby the controller 70 executes the processing shown in FIG. 9.

(S51: Project Fixation Target)

First, the controller 70 controls the fixation projection system (not shown) to project the fixation target on a predetermined projection position deviated from the measurement optical axis of the optical system of the refraction measurement unit 20 on the fundus Ef (peripheral fixation). The projection position of the fixation target is set so that the measurement optical axis is arranged in the peripheral region outside the central region including the fovea of the subject's eye E.

(S52: Perform Objective Refraction Measurement)

Next, the controller 70 controls the refraction measurement unit 20 to perform objective refraction measurement with the fixation target projected on the projection position off the measurement optical axis of the optical system of the refraction measurement unit 20 on the fundus Ef, in the same way as in step S42. Thereby, the ring pattern image is acquired.

(S53: Perform OCT Measurement)

Subsequently, the controller 70 controls the OCT unit 30 to perform OCT measurement (OCT scan) with the fixation target projected on the projection position off the measurement optical axis of the optical system of the refraction measurement unit 20 (OCT unit 30), in the same way as in step S43. In step S53, for example, the first scan and the second scan in a direction orthogonal to the first scan are performed. Here, the first scan is a scan in a direction approximately parallel to a direction connecting the fovea and the projection position of the fixation target. That is, the x-shaped radial scan is performed, or the cross scan that rotates corresponding to the projection position of the fixation target is performed. Thereby, the B-scan images can be acquired along the tangential plane and the sagittal plane.

(S54: Perform Segmentation Processing)

Next, the analyzer 61 specifies a predetermined layer region by performing segmentation processing in the same way as in step S4 and acquires a Hight data [pixel] of the layer region in the B-scan image, for each of the horizontal and vertical B-scan images acquired in step S53. For example, the predetermined layer region is the OS-RPE boundary surface.

(S55: Specify Fundus Tilt Angle)

Next, in the same way as in step S45, the analyzer 61 acquired the distance [mm] of the Height data using the pixel spacing correction value [mm/pixel].

The analyzer 61 calculates a tilt angle θh of for the B-scan image in the horizontal direction and a tilt angle θv of the fundus plane Each for the B-scan, in the same way as in step S45.

(S56: Calculate Dioptric Power in Central Region)

Next, for the horizontal and vertical directions respectively, the calculator 63 corrects the ring pattern image obtained in step S52 in accordance with the tilt angles θh and θv of the fundus plane specified in step S55, in the same way as in step S46. The calculator 63 performs ellipse approximation on the corrected ring pattern image, and obtains the dioptric power using the obtained elliptical shape by a known method.

This terminates the operation of the ophthalmic apparatus according to the sixth embodiment (END).

Seventh Embodiment

In the first to the sixth embodiments, the case of calculating the dioptric power in the peripheral region outside the central region including the fovea in the fundus of the subject's eye has been mainly described. In the seventh embodiment, information for grasping distribution of two or more calculated dioptric powers at two or more positions in the peripheral region is generated.

Examples of the distribution information include information representing the dioptric power for each position and information representing the statistics of the two or more dioptric powers for each block region having a predetermined size or a predetermined shape. Examples of the statistics include an average, a maximum value, a minimum value, a median, a mode, a variance, and a standard deviation. In some embodiments, the distribution information is generated in the distribution table form. In some embodiments, the distribution information is generated in the map format.

The dioptric power at each of the two or more positions in the peripheral region can be calculated using any of the methods in the first to the sixth embodiments. In the following, for convenience of explanation, the ophthalmic apparatus according to the seventh embodiment will be described below in the case of generating the distribution information on the dioptric power in the peripheral region using the method of the first embodiment. However, the methods of the second to the sixth embodiments can be applied to generate the distribution information according to the seventh embodiment in the same way.

Figure 10:
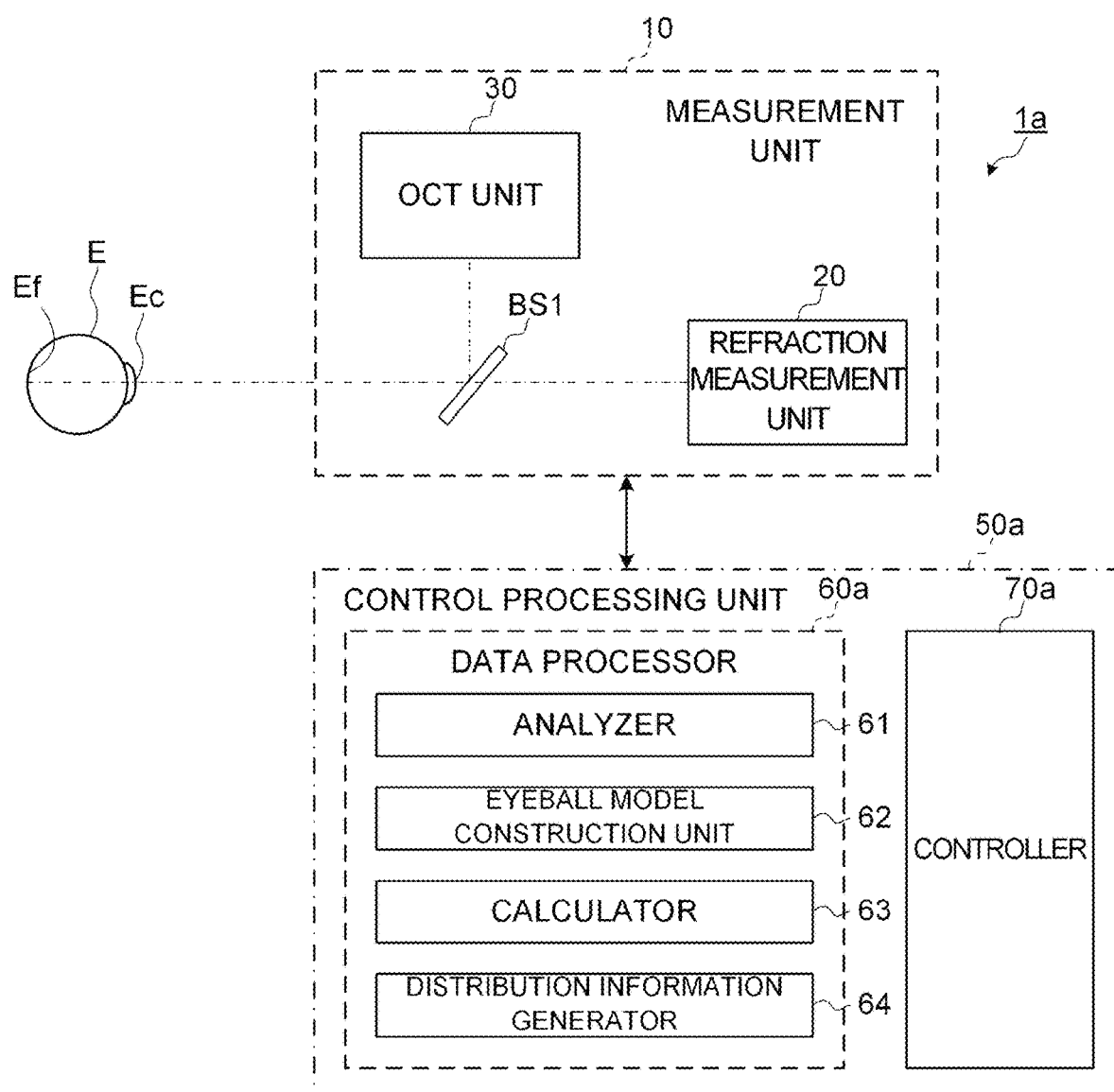
FIG. 10 is a schematic diagram illustrating an example of a configuration of the ophthalmic apparatus according to a seventh embodiment.

FIG. 10 shows an example of a configuration of the ophthalmic apparatus according to the seventh embodiment. In FIG. 10, like reference numerals designate like parts as in FIG. 1, and the same description may not be repeated.

The configuration of the ophthalmic apparatus 1a according to the seventh embodiment differs from that of the ophthalmic apparatus 1 according to the first embodiment mainly in that a control processing unit 50a is provided in place of the control processing unit 50. The difference between the control processing unit 50a and the control processing unit 50 is mainly that the data processor 60a is provided in place of the data processor 60. The data processor 60a differs from the data processor 60 in that a distribution information generator 64 is added to the configuration of the data processor 60.

The distribution information generator 64 generates distribution information on the dioptric powers, based on each of two or more positions in the peripheral region of the central region including the fovea of the subject's eye E and the dioptric power at each position calculated by the calculator 63. That is, the distribution information generator 64 generates the distribution information associating the dioptric power at each position of the two or more positions in the peripheral region with the each position. Here, the dioptric power is obtained in the same way as in the first embodiment. In some embodiments, the distribution information generator 64 generates the distribution information on the dioptric power in the peripheral region and the dioptric powers in at least a part of the central region and. In other words, the peripheral region in that the distribution information on the dioptric powers is generated by the distribution information generator 64 may include at least a part of the central region.

For example, the OCT unit 30 performs the radial scan centered on a reference position in the fundus Ef of the subject's eye E. Examples of the reference position include the fovea and a position in the central region including the fovea. The analyzer 61 obtains the dioptric power in the peripheral region in the same way as in the first embodiment, for each of the OCT data in a plurality of meridian directions acquired by performing the radial scan. At this time, by performing ray tracing processing on the measurement light entering the cornea at a predetermined incident angle using the eyeball model obtained by modeling the eyeball in the same way as in the first embodiment, the dioptric power in the peripheral region can be obtained for the A-line corresponding to the incident angle. By performing the ray tracing processing in the same way as described above for each of a plurality of incident angles within a predetermined incident angle range, the dioptric powers can be obtained at a plurality of positions along a single meridian direction in the peripheral region. This processing is repeated for the number of scan lines in the meridian direction.

In addition to the control contents by the controller 70, the controller 70a can control the distribution information generator 64 and control the output of the distribution information generated by the distribution information generator 64. For example, the controller 70a controls the display device (not shown) to display the distribution information generated by the distribution information generator 64. In some embodiments, the controller 70a displays the OCT image acquired by the OCT unit 30 and the distribution information on the same screen in the display device. In some embodiments, the controller 70a superimposes the distribution information on the OCT image and displays the OCT image that the distribution information has been superimposed on the display device. Examples of the OCT image include a front image of the fundus Ef. In some embodiments, the front image of the fundus Ef is an image acquired using an imaging optical system (not shown). Examples of the imaging optical system includes a fundus camera.

Operation Example

The operation of the ophthalmic apparatus 1a according to the seventh embodiment will be described.

Figure 11:
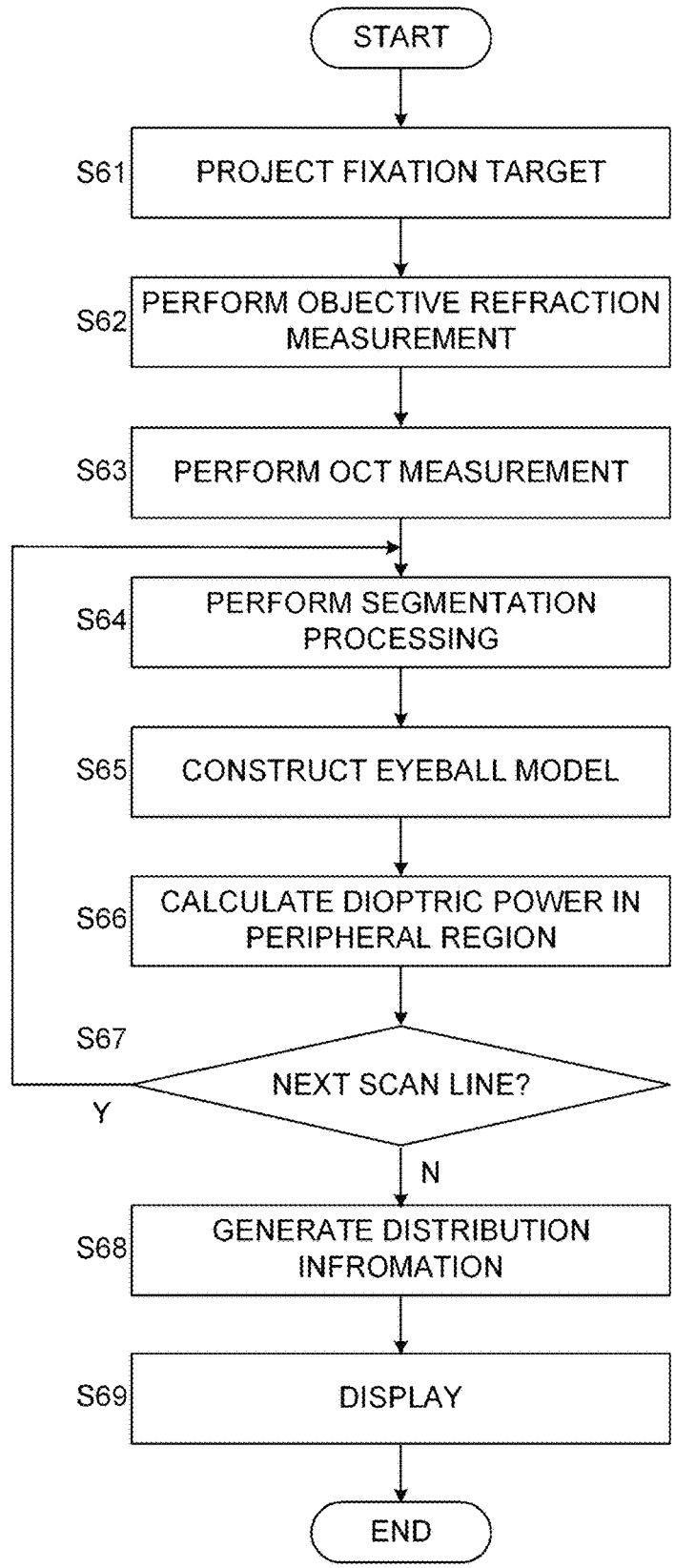
FIG. 11 is a flow chart illustrating an example of an operation of the ophthalmic apparatus according to the seventh embodiment.

FIG. 11 illustrates an example of the operation of the ophthalmic apparatus 1a. FIG. 11 represents a flowchart of an example of the operation of the ophthalmic apparatus 1a. The storage unit in the controller 70a stores the computer program for realizing the processing shown in FIG. 11. The controller 70a operates according to the computer program, and thereby the controller 70a executes the processing shown in FIG. 11.

(S61: Project Fixation Target)

First, in the same way as in step S1, the controller 70a controls the fixation projection system (not shown) to project the fixation target on the measurement optical axis of the optical system of the refraction measurement unit 20.

(S62: Perform Objective Refraction Measurement)

Next, in the same way as in step S2, the controller 70a controls the refraction measurement unit 20 to perform objective refraction measurement with the fixation target projected on the measurement optical axis of the optical system of the refraction measurement unit 20.

(S63: Perform OCT measurement)

Subsequently, in the same way as in step S3, the controller 70a controls the OCT unit 30 to perform OCT measurement with the fixation target projected on the measurement optical axis of the optical system of the refraction measurement unit 20 (OCT unit 30). In step S63, the radial scan centered on the central region is performed, for example.

Further, in step S63, the controller 70a can perform the OCT scan in a direction orthogonal to at least one of a plurality of meridian directions of the radial scan.

(S64: Perform Segmentation Processing)

Next, the analyzer 61 specifies the predetermined layer region by performing segmentation processing in the same way as in step S4 and acquires the Hight data [pixel] of the layer region in the B-scan image, for the B-scan image obtained by performing the scan in a single meridian direction of the radial scan performed in step S63.

(S65: Construct Eyeball Model)

The analyzer 61 constructs the eyeball model, in the same way as in step S5.

(S66: Calculate Dioptric Power in Peripheral Region)

Next, in the same way as in step S6, the calculator 63 calculates the dioptric power in the peripheral region based on the eyeball model constructed in step S65. By performing the ray tracing processing in the same way as described above for each of a plurality of incident angles within a predetermined incident angle range, the calculator 63 obtains the dioptric powers at a plurality of positions along a single meridian direction in the peripheral region. Here, the predetermined incident angle range is uniquely determined by the arrangement of the optical system and the control contents for the optical system.

(S67: Next Scan Line?)

The controller 70a determines whether or not the calculation processing of the dioptric power in the peripheral region is to be performed for the next scan line. For example, the controller 70a determines whether or not the calculation processing of the dioptric power in the peripheral region is to be performed for the next scan line from the number of line scans in the meridian directions constituting the radial scan performed in step S63.

When it is determined to be performed the calculation processing of the dioptric power in the peripheral region for the next scan line (S67: Y), the operation of the ophthalmic apparatus 1a proceeds to step S64. When it is determined not to be performed the calculation processing of the dioptric power in the peripheral region for the next scan line (S67: N), the operation of the ophthalmic apparatus 1a proceeds to step S68.

(S68: Generate Distribution Information)

When it is determined not to be performed the calculation processing of the dioptric power in the peripheral region for the next scan line in step S67 (S67: N), the controller 70a controls the distribution information generator 64 to generate the distribution information representing the distribution of the dioptric powers at positions in the peripheral region obtained by repeatedly performing the processes in steps S64 to S66.

The distribution information generator 64 performs the ray tracing processing for each of the incident angles of the measurement light incident on the cornea within the predetermined incident angle range, and generates the distribution information associating the incident position of the measurement light (position of the A-line) on the fundus Ef with the dioptric power at the incident position, as described above.

Figure 12:
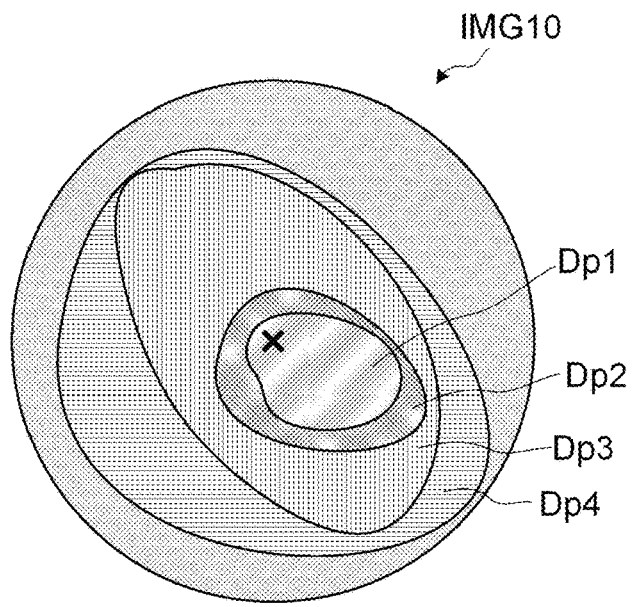
FIG. 12 is a schematic diagram for explaining the operation of the ophthalmic apparatus according to the seventh embodiment.

FIG. 12 schematically shows an example of the distribution information generated by the distribution information generator 64. FIG. 12 represents an example of a dioptric power map with the distribution information expressed in the map format.

The dioptric power map shown in FIG. 12 represents a two-dimensional distribution of the dioptric powers at the positions in the central region CF including the fovea and the peripheral region of the central region CF on the fundus Ef. For example, in the dioptric power map, each of the regions having the dioptric powers $Dp1$, $Dp2$, $Dp3$, $Dp4$, . . . is identifiably represented. In some embodiments, each of the dioptric powers $Dp1$, $Dp2$, $Dp3$, $Dp4$, . . . is a representative value of the dioptric powers within a predetermined range. For example, the region having the dioptric power $Dp1$ may be a region the dioptric power in range of $(Dp1-\Delta p) \leq Dp1 \leq (Dp+\Delta q)$ ($\Delta p$ and $\Delta q$ are real numbers).

In some embodiments, a region having a predetermined range including 0D (diopter) is represented in green. In this case, the region having a dioptric power on the near-sighted side relative to the predetermined range including 0D is identifiably represented using warm colors varying in steps according to the dioptric power. The region having a dioptric power on the far-sighted side relative to the predetermined range including 0D is identifiably represented using cool colors varying in steps according to the dioptric power. In other words, the distribution of the dioptric powers is represented based on the absolute values of the dioptric powers.

In some embodiments, a predetermined region including a reference position on the fundus Ef is represented in green. In this case, the region having a dioptric power on the near-sighted side relative to the dioptric power in the predetermined region is identifiably represented using warm colors varying in steps according to the dioptric power. The region having a dioptric power on the far-sighted side relative to the dioptric power in the predetermined region identifiably represented using cool colors varying in steps according to the dioptric power. In other words, the distribution of the dioptric powers is represented based on the relative value to the dioptric power at the reference position.

In some embodiments, a region including the central region is represented in green. Here, the central region includes the fovea. In this case, the region having a high dioptric power relative to the region including the central region, the central region including the fovea, is identifiably represented using warm colors varying in steps according to the dioptric power. The region having a low dioptric power relative to the region including the central region, the central region including the fovea, is identifiably represented using cool colors varying in steps according to the dioptric power. In other words, the distribution of the dioptric powers is represented based on the relative value to the dioptric power at the central region.

By representing the dioptric power map in any one of the above modes, the entire map can be avoided being represented using the same color. Thereby, the distribution of the dioptric powers can be easily grasped. In some embodiments, the dioptric power map is represented in any of the above modes designated by the user.

(S69: Display)

Next, the controller 70*a* controls the display device (not shown) to display the distribution information generated in step S68. For example, the image IMG 10 with the dioptric power map show in FIG. 12 is identifiably displayed on the display device in any one of the modes described above. Thereby, the distribution of the dioptric powers in the peripheral region (or the central region and the peripheral region) can be easily grasped.

Figure 13:
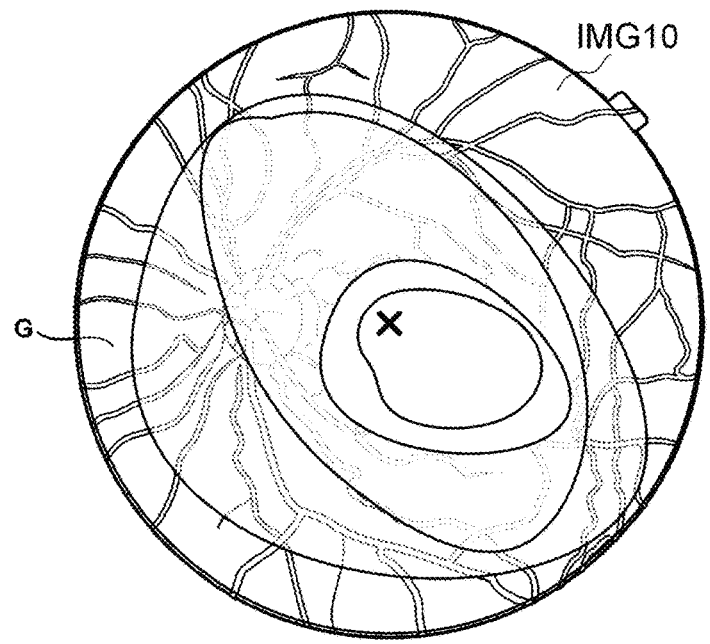
FIG. 13 is a schematic diagram for explaining the operation of the ophthalmic apparatus according to the seventh embodiment.

In some embodiments, the controller 70*a* superimposes the image IMG10 on the fundus image G and displays the fundus image G that the image IMG10 has been superimposed, as shown in FIG. 13. Here, the fundus image G is the front image of the fundus Ef. On the image IMG10, the dioptric power map shown in FIG. 12 is drawn. It should be noted that the identification display of each region in the dioptric power is omitted in FIG. 13. In this case, the controller 70*a* displays the fundus image G and the image IMG10 on the display device, the fundus image G and the image IMG10 having been performed position matching by the data processor 60*a*. In some embodiments, the data processor 60*a* performs position matching on the fundus image G and the image IMG10 so as to cancel a displacement between the position of the optical axis for acquiring the fundus image G and the position of the optical axis of the OCT unit 30. Examples of the optical system for acquiring the fundus image G include an imaging optical system (not shown).

This terminates the operation of the ophthalmic apparatus 1*a* (END).

It should be noted that in step S63 of FIG. 11, at least one line scan may be performed instead of the radial scan, and the distribution information may be generated based on the obtained scan results.

In some embodiments, the controller 70*a* specifies a position designated by the user on the image shown in FIG. 12 or FIG. 13 (or on the screen of the display device), and displays the B-scan image passing through the specified position on the display device. In some embodiments, the controller 70*a* displays the B-scan image passing through the position, the position being designated by the user, and the fovea on the display device. The B-scan image is an image that has already been acquired in the OCT measurement performed in step S63 of FIG. 11, for example. Thereby, the user can easily check the tomographic image at the site of interest by referring to the dioptric power map.

In some embodiments, the data processor 60*a* specifies a characteristic region in the dioptric power map. And then, the controller 70*a* displays the dioptric power map with the specified characteristic region identifiable on the display device (for example, highlighting). Examples of the characteristic region in the dioptric power map include a region with maximum dioptric power, a region with minimum dioptric power, a region with average dioptric power, a region with mode of the dioptric power, a region with median of the dioptric power, a region with large changes in dioptric power relative to adjacent regions, a region with small changes in dioptric power relative to adjacent regions.

[Effects]

The ophthalmic apparatus according to the embodiments will be described.

An ophthalmic apparatus (1, 1*a*) according to some embodiments includes an acquisition unit (measurement unit 10), an OCT unit (30), an analyzer (61), and a calculator (63). The acquiring unit is configured to acquire a dioptric power in a first region (central region) including a fovea of a subject's eye (E). The OCT unit is configured to acquire OCT data of a fundus (Ef) of the subject's eye using optical coherence tomography. The analyzer is configured to specify a shape of the fundus by analyzing the OCT data. The calculator is configured to calculate a dioptric power in a peripheral region of the first region of the fundus based on the dioptric power in the first region and the shape of the fundus.

According to such a configuration, the dioptric power in the peripheral region of the first region is calculated in accordance with the shape of the fundus. Thereby, the dioptric power in the peripheral region can be acquired with high accuracy without being affected by the shape of the fundus. Thus, the ophthalmic apparatus capable of acquiring the dioptric power in the peripheral region available for high performance refractive correction can be provided.

In some embodiments, the calculator is configured to calculate the dioptric power in the peripheral region using a parameter (parameter of the eyeball model) representing optical characteristics of an eyeball.

According to such a configuration, further, the dioptric power in the peripheral region is calculated using the parameter representing the optical characteristics of the eyeball. Thereby, the dioptric power in the peripheral region can be acquired with even higher accuracy.

In some embodiments, the parameter includes axial length data (measurement value of the axial length) acquired by measuring the subject's eye.

According to such a configuration, the dioptric power in the peripheral region can be calculated by reflecting the measurement value of the axial length of the subject. Thereby, the dioptric power in the peripheral region can be acquired with even higher accuracy.

In some embodiments, the parameter includes corneal shape data (measurement value of the corneal curvature radius, measurement value of the corneal thickness) acquired by measuring the subject's eye.

According to such a configuration, the dioptric power in the peripheral region can be calculated by reflecting the measurement value of the corneal shape of the subject. Thereby, the dioptric power in the peripheral region can be acquired with even higher accuracy.

In some embodiments, the parameter includes at least one of anterior chamber depth data (measurement value of the anterior chamber depth) acquired by measuring the subject's eye and crystalline lens shape data (measurement value of the curvature of the crystalline lens, measurement value of the thickness of the crystalline lens) acquired by measuring the subject's eye.

According to such a configuration, the dioptric power in the peripheral region can be calculated by reflecting the measurement value of at least one of the anterior chamber depth and the crystalline lens shape of the subject. Thereby, the dioptric power in the peripheral region can be acquired with even higher accuracy.

In some embodiments, the acquisition unit includes a refraction measurement unit (20) configured to obtain the dioptric power by projecting light onto the first region and detecting returning light of the projected light.

According to such a configuration, the ophthalmic apparatus capable of performing objective refraction measurement and of measuring the dioptric power in the peripheral region with high accuracy can be provided.

An ophthalmic apparatus (1, 1*a*) includes a refraction measurement unit (20), an OCT unit (30), an analyzer (61), and a calculator (63). The refraction measurement unit is configured to objectively measure a dioptric power in a predetermined region (central region or peripheral region)

on a fundus (Ef) of a subject's eye (E). The OCT unit is configured to acquire OCT data of the fundus using optical coherence tomography. The analyzer is configured to specify a shape of the fundus by analyzing the OCT data. The calculator is configured to calculate the dioptric power in the predetermined region on the fundus based on the shape of the fundus.

According to such a configuration, the dioptric power in the predetermined region of fundus is calculated in accordance with the shape of the fundus. Thereby, the dioptric power in the predetermined region can be acquired with high accuracy without being affected by the shape of the fundus.

In some embodiments, the predetermined region is a region including a fovea.

According to such a configuration, the dioptric power in the central region of the fundus, the central region including the fovea, can be accurately acquired.

In some embodiments, the predetermined region is a peripheral region of a region including a fovea.

According to such a configuration, the dioptric power in the peripheral region of the central region of the fundus, the central region including the fovea, can be accurately acquired. The dioptric power in the peripheral region can be used for advanced refractive correction.

In some embodiments, the refraction measurement unit includes an optical system (projection system, light receiving system) configured to project a ring-shaped measurement pattern onto the subject's eye and to detect returning light of the measurement pattern.

According to such a configuration, the ophthalmic apparatus capable of performing objective refraction measurement and of measuring the dioptric power in the predetermined region without being affected by the shape of the fundus with high accuracy can be provided.

In some embodiments, the analyzer is configured to specify a tilt angle of a predetermined layer region in the fundus with respect to a predetermined reference direction, and the calculator is configured to calculate the dioptric power in the predetermined region based on the tilt angle.

According to such a configuration, the tilt angle of the predetermined layer region of the fundus with respect to the predetermined reference direction is specified as the shape of the fundus. Thereby, the dioptric power in the predetermined region of the fundus can be calculated in accordance with the shape of the fundus, with a simple process.

In some embodiments, the calculator is configured to calculate the dioptric power in the predetermined region by correcting a major axis and a minor axis of a ring pattern image obtained based on the returning light detected by the optical system, according to the tilt angle.

According to such a configuration, the dioptric power in the predetermined region is obtained by correcting the major axis and the minor axis of the acquired ring pattern image in accordance with the tilt angle. Thereby, the dioptric power in the predetermined region of the fundus can be calculated in accordance with the shape of the fundus, with a simple process.

In some embodiments, the OCT unit is configured to acquire the OCT data by performing a radial scan on the predetermined region.

According to such a configuration, the tile angle can be specified for a plurality of directions. Thereby, the dioptric power in the predetermined region of the fundus can be calculated with high accuracy.

In some embodiments, the OCT unit is configured to acquire the OCT data by performing a first scan in a horizontal direction and a second scan in a vertical direction intersecting the first scan on the predetermined region.

According to such a configuration, the tilt angle can be specified for the horizontal direction and the vertical direction. Thereby, the dioptric power in the predetermined region of the fundus can be calculated with high accuracy.

In some embodiments, when a fixation target is projected so that a measurement optical axis is located in a peripheral region of a region including a fovea in the fundus, the OCT unit is configured to acquire the OCT data by performing a first scan and a second scan in a direction orthogonal to the first scan, the first scan being a scan in a direction approximately parallel to a direction connecting the fovea and a projection position of the fixation target.

According to such a configuration, the tile angle can be specified for a plurality of directions even if the fixation target is projected onto the position off the measurement optical axis. Thereby, the dioptric power in the predetermined region of the fundus can be calculated with high accuracy.

The ophthalmic apparatus according to some embodiments further includes a distribution information generator (64) configured to generate distribution information on dioptric powers, based on each of two or more positions in the peripheral region of a region including a fovea of the subject's eye and the dioptric power calculated by the calculator.

According to such a configuration, the peripheral defocus state of the fundus considered to be one of the factors of the myopia progression can be easily grasped.

The ophthalmic apparatus according to some embodiments further includes a controller (70a) configured to superimpose the distribution information on a front image of the fundus and to display the front image that the distribution information has been superimposed.

According to such a configuration, the peripheral defocus state of the fundus of the subject's eye can be grasped specifically.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute the method of controlling the ophthalmic apparatus is provided. Such a program can be stored in any computer-readable recording medium (for example, a non-transitory computer readable medium). Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
an acquiring unit including a refractometer and configured to acquire a dioptric power in a first region including a fovea of a subject's eye;
an Optical Coherence Tomography (OCT) unit including an OCT scanner and configured to acquire OCT data of a fundus of the subject's eye using optical coherence tomography;
processing circuitry configured as an analyzer configured to specify a shape of the fundus by analyzing the OCT data; and
the processing circuitry further configured as a calculator configured to calculate a dioptric power in a peripheral region of the first region of the fundus based on the dioptric power in the first region and the shape of the fundus,
wherein the shape of the fundus indicates a difference in depth position between a central region on the fundus and a peripheral region on the fundus.

2. The ophthalmic apparatus of claim 1, wherein the calculator is configured to calculate the dioptric power in the peripheral region using a parameter representing optical characteristics of an eyeball.

3. The ophthalmic apparatus of claim 2, wherein the parameter includes axial length data acquired by measuring the subject's eye.

4. The ophthalmic apparatus of claim 2, wherein the parameter includes corneal shape data acquired by measuring the subject's eye.

5. The ophthalmic apparatus of claim 2, wherein the parameter includes at least one of anterior chamber depth data acquired by measuring the subject's eye and crystalline lens shape data acquired by measuring the subject's eye.

6. The ophthalmic apparatus of claim 1, wherein the acquisition unit includes a refraction measurement unit configured to obtain the dioptric power by projecting light onto the first region and detecting returning light of the projected light.

7. An ophthalmic apparatus, comprising:
a refraction measurement unit including a refractometer and configured to objectively measure a dioptric power in a predetermined region on a fundus of a subject's eye;
an Optical Coherence Tomography (OCT) unit including an OCT scanner and configured to acquire OCT data of the fundus using optical coherence tomography;
processing circuitry configured as an analyzer configured to specify a shape of the fundus by analyzing the OCT data; and
the processing circuitry further configured as a calculator configured to calculate the dioptric power in the predetermined region on the fundus based on the shape of the fundus,
wherein the shape of the fundus indicates a difference in depth position between a central region on the fundus and the peripheral region on the fundus.

8. The ophthalmic apparatus of claim 7, wherein the predetermined region is a region including a fovea.

9. The ophthalmic apparatus of claim 7, wherein the predetermined region is a peripheral region of a region including a fovea.

10. The ophthalmic apparatus of claim 7, wherein the refraction measurement unit includes an optical system configured to project a ring-shaped measurement pattern onto the subject's eye and to detect returning light of the measurement pattern.

11. The ophthalmic apparatus of claim 10, wherein the analyzer is configured to specify a tilt angle of a predetermined layer region in the fundus with respect to a predetermined reference direction, and
the calculator is configured to calculate the dioptric power in the predetermined region based on the tilt angle.

12. The ophthalmic apparatus of claim 11, wherein the calculator is configured to calculate the dioptric power in the predetermined region by correcting a major axis and a minor axis of a ring pattern image obtained based on the returning light detected by the optical system, according to the tilt angle.

13. The ophthalmic apparatus of claim 10, wherein the OCT unit is configured to acquire the OCT data by performing a radial scan on the predetermined region.

14. The ophthalmic apparatus of claim 10, wherein the OCT unit is configured to acquire the OCT data by performing a first scan in a horizontal direction and a second scan in a vertical direction intersecting the first scan on the predetermined region.

15. The ophthalmic apparatus of claim 10, wherein when a fixation target is projected so that a measurement optical axis is located in a peripheral region of a region including a fovea in the fundus, the OCT unit is configured to acquire the OCT data by performing a first scan and a second scan in a direction orthogonal to the first scan, the first scan being a scan in a direction approximately parallel to a direction connecting the fovea and a projection position of the fixation target.

16. The ophthalmic apparatus of claim 1, further comprising
a distribution information generator configured to generate distribution information on dioptric powers, based on each of two or more positions in the peripheral region of a region including a fovea of the subject's eye and the dioptric power calculated by the calculator.

17. The ophthalmic apparatus of claim 16, further comprising
a controller configured to superimpose the distribution information on a front image of the fundus and to display the front image that the distribution information has been superimposed.

18. The ophthalmic apparatus of claim 15, further comprising
a distribution information generator configured to generate distribution information on dioptric powers, based on each of two or more positions in the peripheral region of a region including a fovea of the subject's eye and the dioptric power calculated by the calculator.

19. The ophthalmic apparatus of claim 18, further comprising
a controller configured to superimpose the distribution information on a front image of the fundus and to display the front image that the distribution information has been superimposed.

* * * * *